(12) United States Patent
Siedenburg et al.

(10) Patent No.: US 11,957,504 B2
(45) Date of Patent: Apr. 16, 2024

(54) PATIENT MONITORING AND TREATMENT SYSTEMS AND METHODS

(71) Applicant: Stryker Corporation, Kalamazoo, MI (US)

(72) Inventors: Clinton T. Siedenburg, Everett, WA (US); Arthur T. Lounsbery, Woodinville, WA (US); Mitchell A. Smith, Sammamish, WA (US); Robert G. Walker, Seattle, WA (US)

(73) Assignee: Stryker Corporation, Kalamazoo, MI (US)

( * ) Notice: Subject to any disclaimer, the term of this patent is extended or adjusted under 35 U.S.C. 154(b) by 318 days.

(21) Appl. No.: 17/328,928

(22) Filed: May 24, 2021

(65) Prior Publication Data

US 2021/0275131 A1 Sep. 9, 2021

Related U.S. Application Data

(63) Continuation of application No. 16/013,484, filed on Jun. 20, 2018, now Pat. No. 11,013,488, and a
(Continued)

(51) Int. Cl.
*A61B 5/00* (2006.01)
*A61B 5/02* (2006.01)
(Continued)

(52) U.S. Cl.
CPC .............. *A61B 8/04* (2013.01); *A61B 5/0022* (2013.01); *A61B 5/0059* (2013.01);
(Continued)

(58) Field of Classification Search
CPC ........... A61B 8/06; A61B 8/4416; A61B 5/08; A61B 5/029; A61B 5/02125;
(Continued)

(56) References Cited

U.S. PATENT DOCUMENTS 5,535,747 A * 7/1996 Katakura ................. A61B 8/04
600/438
2005/0228282 A1 10/2005 Wang et al.
(Continued)

OTHER PUBLICATIONS

Office Action for U.S. Appl. No. 16/013,627, dated Jun. 6, 2023, Clinton T. Siedenburg, "Patient Monitoring and Treatment Systems and Methods", 39 pages.
(Continued)

*Primary Examiner* — Rex R Holmes
(74) *Attorney, Agent, or Firm* — Lee & Hayes, P.C.

(57) ABSTRACT

Non-invasive blood pressure (NIBP) systems and methods are disclosed that measure a blood pressure, and in some examples a beat-to-beat blood pressure, of a patient without restricting blood flow. The NIBP systems determine an efficacy of administered cardiopulmonary resuscitation (CPR) to the patient based on the measured blood pressure and are able to optionally output the CPR efficacy or generate user prompts based on the CPR efficacy. Further, the disclosed NIBP systems can generate user instructions to administer further treatment to the patient based on the CPR efficacy.

19 Claims, 10 Drawing Sheets

Related U.S. Application Data continuation of application No. 16/013,627, filed on Jun. 20, 2018.

(60) Provisional application No. 62/524,088, filed on Jun. 23, 2017.

(51) Int. Cl.
| | |
|---|---|
| *A61B 5/0205* | (2006.01) |
| *A61B 5/021* | (2006.01) |
| *A61B 5/1455* | (2006.01) |
| *A61B 5/349* | (2021.01) |
| *A61B 8/00* | (2006.01) |
| *A61B 8/04* | (2006.01) |
| *A61B 8/08* | (2006.01) |
| *A61H 31/00* | (2006.01) |
| *A61B 5/0245* | (2006.01) |
| *A61B 5/029* | (2006.01) |
| *A61B 5/0531* | (2021.01) |
| *A61B 5/08* | (2006.01) |
| *A61B 5/083* | (2006.01) |
| *A61B 8/06* | (2006.01) |

(52) U.S. Cl.
CPC ........ *A61B 5/0064* (2013.01); *A61B 5/02028* (2013.01); *A61B 5/0205* (2013.01); *A61B 5/02108* (2013.01); *A61B 5/14551* (2013.01); *A61B 5/349* (2021.01); *A61B 5/6833* (2013.01); *A61B 8/4236* (2013.01); *A61B 8/5223* (2013.01); *A61H 31/005* (2013.01); A61B 5/02007 (2013.01); A61B 5/02125 (2013.01); A61B 5/0245 (2013.01); A61B 5/029 (2013.01); A61B 5/0531 (2013.01); A61B 5/08 (2013.01); A61B 5/0836 (2013.01); A61B 5/14552 (2013.01); A61B 8/06 (2013.01); A61B 8/4416 (2013.01); A61B 8/488 (2013.01); A61B 2560/0214 (2013.01); A61B 2560/0252 (2013.01); A61B 2562/242 (2013.01); A61H 2201/165 (2013.01); A61H 2201/168 (2013.01); A61H 2201/5043 (2013.01); A61H 2201/5058 (2013.01); A61H 2201/5082 (2013.01); A61H 2201/5084 (2013.01); A61H 2201/5097 (2013.01); A61H 2230/045 (2013.01); A61H 2230/208 (2013.01); A61H 2230/255 (2013.01); A61H 2230/405 (2013.01)

(58) Field of Classification Search
CPC .............. A61B 5/02007; A61B 5/0531; A61B 2560/0214; A61B 2560/0252; A61B 5/0836; A61B 5/14552; A61B 5/0245; A61B 2562/242; A61B 8/488; A61B 8/04; A61B 8/5223; A61B 8/4236; A61B 5/14551; A61B 5/0452; A61B 5/0205; A61B 5/02028; A61B 5/0059; A61B 5/0064; A61B 5/0022; A61B 5/6833; A61B 5/02108; A61H 2230/405; A61H 2230/255; A61H 2230/208; A61H 2230/045; A61H 31/005; A61H 2201/5097; A61H 2201/5084; A61H 2201/168; A61H 2201/5043; A61H 2201/5082; A61H 2201/165; A61H 2201/5058

See application file for complete search history.

(56) References Cited

U.S. PATENT DOCUMENTS

| | | |
|---|---|---|
| 2006/0173514 A1 | 8/2006 | Biel et al. |
| 2006/0211942 A1 | 9/2006 | Hoctor et al. |
| 2007/0010748 A1 | 1/2007 | Rauch et al. |
| 2008/0269818 A1* | 10/2008 | Sullivan ............... A61N 1/3625 607/10 |
| 2010/0022886 A1 | 1/2010 | Ayati et al. |
| 2010/0030020 A1 | 2/2010 | Sanders et al. |
| 2010/0176952 A1 | 7/2010 | Bajcsy et al. |
| 2010/0217102 A1 | 8/2010 | Leboeuf et al. |
| 2011/0009711 A1 | 1/2011 | Nanikashvili et al. |
| 2011/0130669 A1 | 6/2011 | Garner et al. |
| 2015/0169835 A1 | 6/2015 | Hamdan et al. |
| 2016/0007862 A1 | 1/2016 | Ku |
| 2016/0054354 A1 | 2/2016 | Keal et al. |
| 2016/0199251 A1 | 7/2016 | Aelen et al. |
| 2016/0270673 A1* | 9/2016 | Aelen ................ A61B 5/02225 |
| 2017/0000688 A1* | 1/2017 | Kaufman ........... A61B 5/02416 |
| 2017/0209053 A1 | 7/2017 | Pantelopoulos et al. |
| 2017/0354331 A1 | 12/2017 | Borkholder et al. |
| 2018/0199834 A1 | 7/2018 | Siedenburg |
| 2018/0206746 A1 | 7/2018 | Narasimhan et al. |
| 2018/0235567 A1 | 8/2018 | Bezemer et al. |

OTHER PUBLICATIONS

Office Action for U.S. Appl. No. 16/013,627, dated Mar. 2, 2022, Siedenburg, "Patient Monitoring and Treatment Systems and Methods", 26 pages.

Office Action for U.S. Appl. No. 16/013,627, dated Sep. 22, 2022, Siedenburg, "Patient Monitoring and Treatment Systems and Methods", 28 pages.

Office Action for U.S. Appl. No. 16/013,484, dated Aug. 17, 2020, Siedenburg, "Patient Monitoring and Treatment Systems and Methods", 11 pages.

Office Action for U.S. Appl. No. 16/013,484, dated Nov. 14, 2019, Siedenburg, "Patient Monitoring and Treatment Systems and Methods", 9 pages.

Office Action for U.S. Appl. No. 16/013,627, dated Dec. 30, 2020, Siedenburg, "Patient Monitoring and Treatment Systems and Methods", 21 pages.

Office Action for U.S. Appl. No. 16/013,484, dated Apr. 9, 2020, Siedenburg, "Patient Monitoring and Treatment Systems and Methods", 10 pages.

Office Action for U.S. Appl. No. 16/013,627, dated Jul. 15, 2021, Siedenburg, "Patient Monitoring and Treatment Systems and Methods," 27 pages.

* cited by examiner

PATIENT MONITORING AND TREATMENT SYSTEMS AND METHODS

CROSS-REFERENCE TO RELATED APPLICATIONS

This application is a continuation of U.S. patent application Ser. No. 16/013,484, filed on Jun. 20, 2018, entitled "Patient Monitoring and Treatment Systems and Methods," and this application is a continuation of U.S. patent application Ser. No. 16/013,627, filed on Jun. 20, 2018 entitled, "Patient Monitoring and Treatment Systems and Methods," both of which claim the benefit of and priority to U.S. Provisional Patent Application Ser. No. 62/524,088, filed on Jun. 23, 2017, entitled "Noninvasive Blood Pressure (NIBP) Pulse Wave Velocity (PWV) by Ultrasound Sensor," all of which are hereby incorporated by reference in their entirety.

BACKGROUND

Patient monitoring and treatment can involve invasive means that require inserting sensors within a patient to acquire the requisite data, such as a blood pressure of the patient. The blood pressure of a patient is a critical measurement that is used in monitoring and treating the patient. There are two means by which the blood pressure of the patient can be measured, one is invasive and the other is non-invasive. In the invasive means, the blood pressure is obtained by direct measurement, requiring a sensor to be inserted into the circulatory system of the patient to obtain the measurements. In certain situations that require precise, beat-to-beat blood pressure measurements, such as some surgical applications, the invasive means can provide the necessary data. Further, the invasive means can cause discomfort in the patient or the subject for which the blood pressure is being measured. Additionally, there is an increased risk of complications and/or increased expense due to the invasive nature of such blood pressure measurement.

In the non-invasive means, the sensing of the blood pressure is done externally to the patient and tends to only capture peak pressure readings, such as an intra-arterial blood pressure at diastole and systole, which provides little to no information about the patient's blood flow or vessel health. Typically, this involves the application of a cuff about a limb of the patient and the pressurization of the cuff to cut-off circulation through the limb. The pressure applied by the cuff to the limb is slowly reduced and as blood flow is resumed, the blood pressure can be measured based on the pressure remaining in the cuff. This process is often repeated multiple times to ensure an accurate measurement or as a means of monitoring over an extended period of time, with pauses required between measurement instances. While this means is non-invasive, it does require the temporary restriction of circulation in a portion of the patient, which can be damaging to the health of the patient and also requires time for the process to be fully performed. Additionally, such non-invasive blood pressure measurement techniques are sensitive to motion of the patient, accessories to the non-invasive blood pressure equipment being bumped or jostled during patient care or transport, etc., which can result in inaccurate and/or unobtainable blood pressure measurements. In patient transport or emergency situations, the patient and the equipment, such as the hosing, can be subjected to a large amount of motion during time in which an accurate blood pressure measurement can be critical to assess the state of the patient.

As such, there is a need for non-invasive patient monitoring and treatment systems and methods that can provide accurate patient information, such as blood pressure, for use in monitoring and/or treating the patient

DETAILED DESCRIPTION

Non-invasive patient monitoring and treatment systems and methods are described herein. Non-invasive blood pressure (NIBP) measurement systems and/or methods can calculate a blood pressure and/or vessel dynamics of a person. Such data can be used in the monitoring and/or treatment of the person, such as for clinically evaluating a condition, or state, of the person. Additionally, the collected data can be correlated and/or aggregated with other physiological parameter data and/or vital signs of the person. Correlated and/or NIBP data can provide indications of the effectiveness of a treatment of the person, can provide indications of potential changes in the clinical condition/state of the person and/or can provide data to assist with monitoring the clinical condition/state of the person or a change and/or addition in care and/or treatment to be provided to the patient. In an example, the NIBP and/or correlated data can provide indications of the effectiveness of cardiopulmonary resuscitation administration and can also be used to provide feedback to modify or alter the administration of cardiopulmonary resuscitation to improve its effectiveness. Further, conditions and/or ailments of the person can be tracked, or monitored, using the NIBP and/or other physiological and/or vital signs data.

The NIBP data can be collected with the assistance of an NIBP device. The NIBP device can radiate energy into tissues of the person. The radiated energy can reflect from one or more of the tissues, such as flowing blood, and the reflected energy can be detected, or sensed, by a sensor to generate an NIBP signal. The NIBP signal can be processed to calculate the blood pressure and/or vessel dynamics of the person. Additionally, the NIBP device can receive and/or process other vital signs data of the person to assist with monitoring and/or treatment of the person.

Figure 1:
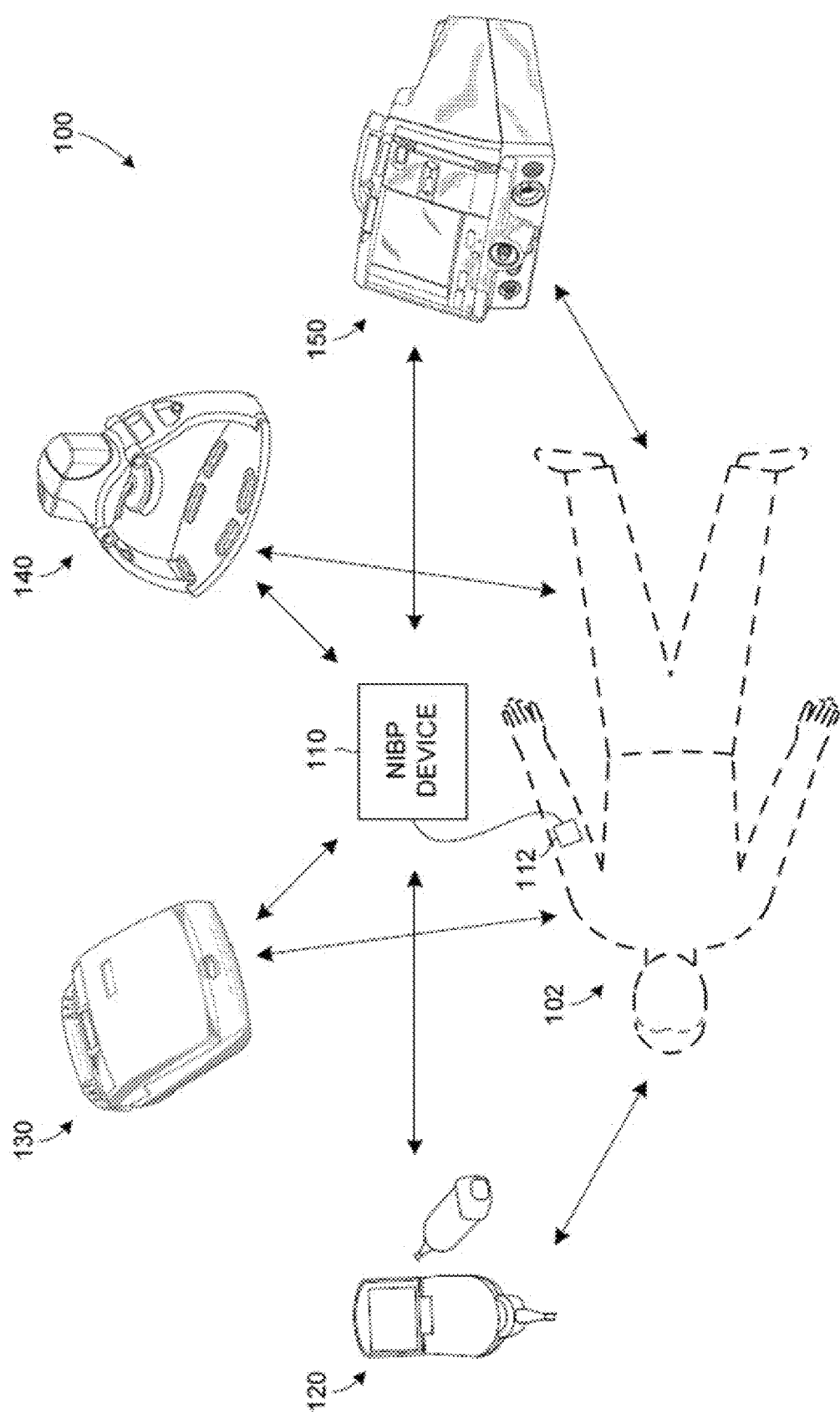
FIG. 1 is an example patient monitoring and/or treatment system.

FIG. 1 illustrates an example patient monitoring and/or treatment system 100. One or more medical devices can be used to monitor and/or treat a patient 102, such as a non-invasive blood pressure (NIBP) device 110, an ultrasound device 120, an automated external defibrillator 130, a chest compression machine (CCM) 140, a monitor/defibrillator 150, and/or other medical, or other, devices/systems.

Data, such as patient vital signs data, acquired/sensed by one of the medical devices can be shared amongst the other devices to assist with the monitoring and/or treatment of the patient 102.

The NIBP device 110 can include an NIBP sensor 112 that can be placed on the patient 102 to generate an NIBP signal, or data, that can be processed by the NIBP device 110 to determine a blood pressure of the patient. The NIBP sensor 112 can radiate energy, such as ultrasound or light, into the tissues of the patient to sense and generate the NIBP signal in response to the reflection of the radiated energy from the tissues of the patient, such as flowing blood. The NIBP device 110 can receive the NIBP signal and determine an instantaneous blood velocity that can be used, with a blood density, pulse wave velocity, and/or other vital signs data, to calculate the blood pressure of the patient 102 and/or one or more vessel dynamics of the patient 102.

The data, such as the calculated blood pressure and/or vessel dynamics, can be communicated by the NIBP device 110 to one or more other devices to assist with monitoring and/or treating the patient 102. For example, the NIBP device 110 can share blood pressure, vessel dynamics and/or other data with an automatic external defibrillator (AED) 130, a chest compression machine (CCM) 140, monitor/defibrillator 150 and/or other devices/systems to assist with one or more patient monitoring and/or treatment tasks, such as patient resuscitation. These other devices can alter their patient monitoring and/or treatment in response to and/or based on the data received from the NIBP device 110.

In another example, one of the other devices/systems, such as the ultrasound device 120 and/or the monitor/defibrillator 150, can radiate energy into the tissues of the patient 102 and the reflected energy therefrom can be detected by a sensor of the NIBP device 110 that is placed on the patient 102. The reflected energy can be sensed by the sensor to generate the NIBP signal that can be processed by the NIBP device 110 to calculate a blood pressure and/or vessel dynamics of the patient 102. Alternatively, or additionally, the functionality and/or features of the NIBP device 110 can be integrated with one or more of the other devices/systems used to monitor and/or treat the patient 102. In such an integration, the NIBP functionality can use, or sense, energy normally radiated into patient tissues by the other device/system to generate the NIBP signal/data.

For example, the NIBP device 110 can be integrated with a standard ultrasound machine. For the integration to function properly, a software update may be needed to configure the standard ultrasound machine to further process the raw NIBP data measured by the NIBP device. The existing hardware and/or software of the standard ultrasound machine, such as the transducers, acquisition sequence, and data processing, can be programmed to become the NIBP device without additional hardware being added. Alternatively, emitter/detector combination hardware of the NIBP device could be added to the standard ultrasound machine, for example, in place of or in addition to the machine's existing scan head. The substitute or replacement emitter/detector combination hardware could be electronically coupled to the transmitter and receiver electronics and processing resources of the standard ultrasound machine. Still further, the NIBP device could also transmit its data, in raw waveform or processed in some form, to the standard ultrasound machine to further process and/or display the resulting NIBP measurements and/or NIBP or other physiological parameter data.

The software update on the standard ultrasound machine can be made to existing equipment so that it functions in the integrated fashion when a NIBP device is connected or discovered. The software update to the standard ultrasound machine can include configuring the standard ultrasound machine to perform such functions as calculating the blood pressure and/or vessel dynamics of the patient from the data provided by the NIBP device, for example, and to operate in a different mode for obtaining the image through ultrasound techniques because the imaging processing required can be different when measuring NIBP using the disclosed techniques than for medical ultrasound imaging typically performed with a standard ultrasound machine. The standard ultrasound machine can be updated in any suitable manner.

In a further example, a single NIBP 110 device can be connected, wired and/or wirelessly, to multiple NIBP sensors 112 placed on one or more patients. The NIBP device 110 can monitor/calculate the blood pressure and/or vessel dynamics of the one or more patients upon which the NIBP sensors 112 are placed. Such an arrangement can assist in mass casualty situations wherein a single NIBP device 110 can monitor multiple patients.

Figure 2:
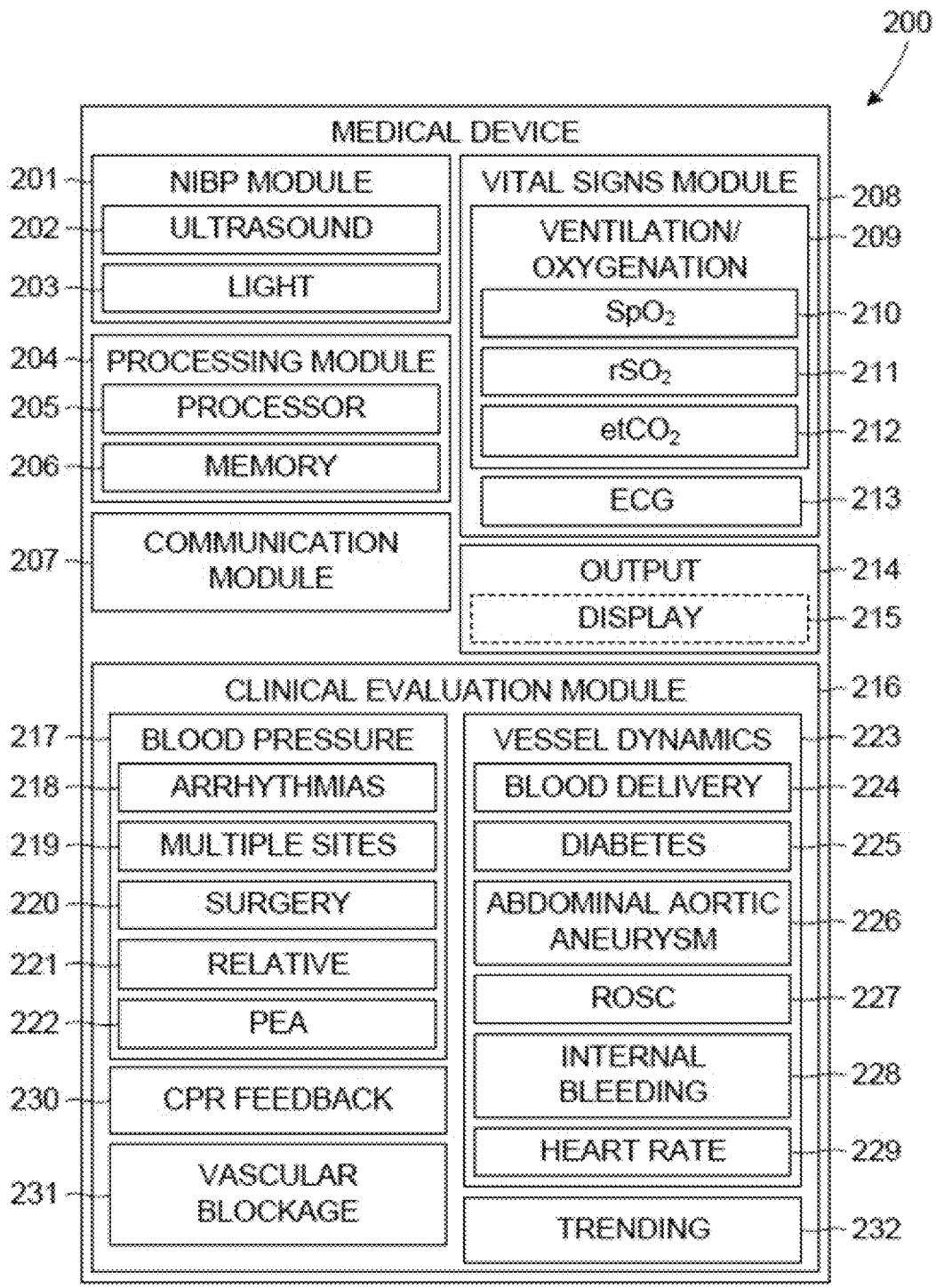
FIG. 2 is a block diagram of an example non-invasive blood pressure (NIBP) device.

FIG. 2 illustrates an example non-invasive blood pressure (NIBP) device 200 that can assist with monitoring and/or treating a patient. The NIBP device 200 can be placed on and/or coupled to a patient, to sense and/or receive vital signs data therefrom, and/or can otherwise receive patient vital signs data and/or any other patient physiological data, to calculate a blood pressure 217 and/or vessel dynamics 223 of the patient. The blood pressure 217, vessel dynamics 223 and/or other vital signs data can assist with evaluating a clinical state of the patient.

An NIBP module 201 of the NIBP device 200 can receive reflected energy, and/or a signal representative thereof, caused by energy, such as ultrasound 202 and/or light 203, radiated and/or transmitted into the tissues of the patient. The NIBP module can process the reflected energy and/or signal to determine a blood velocity and/or pulse wave velocity, which can be used to calculate the blood pressure 217 and/or vessel dynamics 223 of the patient. The NIBP module, and/or an NIBP sensor, can include energy emitters to emit/radiate energy into the tissues of the patient and can include sensors to sense/receive/detect reflected energy. The sensors can generate an NIBP signal that can then be processed by the NIBP module 201 to determine an instantaneous blood velocity, which can be used to calculate the blood pressure and/or vessel dynamics of the patient.

A processing module 204 can control various functions and/or features of the NIBP device 200 and/or can analyze/process data. The processing module 204 can include a processor 205 and memory 206 for storing data and/or instructions for execution by the processor 205. In an example, processing of the NIBP signal can be performed by the processing module 204 to calculate the blood pressure and/or vessel dynamics of the patient. Additionally, the processing module 204 can process other physiological data, such as from a vital signs module 208 and/or other devices/systems, to assist with evaluating a clinical state of the patient.

A communication module 207 can transmit data from and/or receive data to the NIBP device 200 using one or more communication protocols. Communication to/from the NIBP device 200 can be with another device and/or system, such as a patient monitoring and/or treatment device/system. The communication module 207 can transmit data widely, such as via a network and/or the Internet, and/or locally, such as via a Bluetooth, near field communication (NFC), Wi-Fi Direct®, WiGig, cellular, and/or another local network. Additionally, transmissions to/from the communication module 207 can be via a wired and/or a wireless connection.

The vital signs module 208 can receive patient vital signs data from one or more vital signs or other physiological sensors and/or devices/systems and/or can include one or more sensors to sense one or more vital signs or other physiological parameters of the patient. Any patient parameters can be measured, including vital sign(s) and/or any patient physiological parameters. The vital signs and/or patient physiological parameters described in this disclosure include any medical data relating to the patient. FIG. 2 shows a vital signs module 208 by way of example, and the vital signs module 208 could alternatively be identified as a patient physiological parameters module or other patient data module. The vital signs monitored by the vital signs module 208 can include ventilation/oxygenation 209 and/or ECG 213 parameters. The ventilation/oxygenation 209 can include pulse oximetry 210, tissue/regional oximetry 211 and/or end-tidal CO2 212 data. The vital signs data of the vital signs module 208 can be used with the NIBP data to assist with evaluating a clinical state of the patient, such as by a clinical evaluation module 216.

The NIBP device 200 can include an output 214 that can output the blood pressure, vessel dynamics, vital signs and/or physiological parameters, clinical evaluation/clinical state, and/or other data to a user, device and/or system. The user, device and/or system can receive the data from the output to assist with monitoring and/or treating the patient. Optionally, the output 214 can include a display 215 that can display and/or present the data to a user, such as to assist with monitoring and/or treatment of the patient by the user. Other output can also be included such as haptic, auditory, and visual output, for example.

The clinical evaluation module 216 can evaluate a clinical state/condition of the patient based on the NIBP, vital signs and/or other data. One or more clinical states/conditions can be evaluated based on the blood pressure data and other can be based on the vessel dynamics data. Additionally, the clinical evaluation module 216 can provide CPR feedback 230, vascular blockage 231 data, trends 232 and/or other data, based on the NIBP, vital signs and/or other data.

The clinical evaluation module 216 can use blood pressure 217 data to evaluate clinical states/conditions, such as arrhythmias 218, to monitor blood pressure at multiple sites 219 of the patient, monitor blood pressure during surgery 220, monitor relative blood pressure 221, detect pulseless electrical activity (PEA) and/or other states/conditions. The blood pressure 217 monitoring can be continuous, allowing the blood pressure to be monitored throughout the cardiac cycle and beat-to-beat. Rather than typical peak systolic and/or diastolic values, the blood pressure can be monitored on a finer/more granular scale throughout the duration of each cardiac cycle or selected sampling of cardiac cycles. Additionally, or alternatively, the blood pressure can be monitored for an interval(s) and/or monitored spaced apart by an interval(s), allowing for the patient's blood pressure to be monitored over an extended period of time.

To detect/evaluate the patient for arrhythmias 218, the clinical evaluation module 216 can evaluate the continuous blood pressure measurement. Evaluation of the arrhythmia(s) 218 can include characterizing the arrhythmia 218 and/or estimating a severity of the arrhythmia 218. The arrhythmia 218 detection/evaluation can be used by a user, device and/or system to assist with further patient care, such as monitoring/treatment decisions. Additionally, the information can be used to evaluate patients with syncope, such as neurocardiogenic syncope, which can be caused by atrial fibrillation, ventricular fibrillation and/or other arrhythmias. Further, other types of syncope can also be detected and/or evaluated by the clinical evaluation module 216.

Blood pressure of the patient can be monitored simultaneously at multiple sites 218 across the patient's body, allowing for total blood supply to be monitored, evaluated and/or controlled. Multi-site 218 monitoring of blood pressure can be used to monitor a patient during surgery 220 or in an intensive care unit, for example. Some surgeries, such as open heart surgery, can require invasive blood pressure monitoring across one or more sites of the patient's body, which one or more of the disclosed NIBP devices 200 can replace. NIBP sensors and/or devices can be placed at multiple locations of the patient's body to obtain the whole body blood pressure measurement. In the example of multiple NIBP sensors, each sensor can communicate wirelessly to a common NIBP device which can process the received NIBP signals to provide the whole body blood pressure data. The wireless communication can reduce the intrusion of cables within the surgical area. In other surgeries, localized monitoring of the blood pressure around the surgical area can be required and/or desired. Multiple NIBP sensors and/or devices can assist with monitoring the local blood pressure about the surgical area. In the open heart surgery example, the NIBP sensor(s) and/or device can be integrated with one or more surgical tools to monitor blood pressure in various areas of the heart.

Relative 221 blood pressure can also be monitored by the clinical evaluation module 216. Relative changes in blood pressure can be monitored and can trigger alerts when the relative change is outside of a threshold value/range. In an example, changes in pulse pressure can trigger alerts when the difference in systolic and diastolic pressures are too small, too large and/or too varying.

Pulseless electrical activity (PEA) 222 can also be detected based on the blood pressure data and the ECG data 213. The lack of blood pressure combined with ECG data indicating electrical activity can identify the presence of PEA 222.

The clinical evaluation module 216 can use vessel dynamics 223 to assist with evaluating a clinical state/condition of the patient. Blood delivery 224, diabetes 225, abdominal aortic aneurysm 226, Return of Spontaneous Circulation (ROSC) 227, internal bleeding 228, heart rate 229 and/or other clinical states and/or conditions can be evaluated using vessel dynamics 223 data, such as calculated from the NIBP module 201.

Blood delivery 224 can be monitored and/or evaluated by the clinical evaluation module 216. The NIBP module 201 can determine various vessel dynamics, such as blood flow velocity and vessel diameter, which can be used to determine a blood rate and blood delivery volume. Using the blood rate and delivery flow, a low blood flow condition can be identified and/or characterized, such as scored for its severity and/or impact on the patient's physiological state. This information can assist a user, device and/or system with patient monitoring and/or treatment. In some examples, the low blood flow condition and/or the severity score are output to a user in the form of a user prompt or a visual, haptic, or audible alert or indicator. The processing module can determine recommended treatments for the patient based on the low blood flow condition and/or the severity score, which can also be output to the user in any desired form.

The blood delivery 224 can be measured locally on a patient, such as at patient extremities. Additionally, the blood delivery 224 data can assist with identifying/monitoring diabetes 225. Diabetics often suffer from low blood flow to extremities, which can be monitored by the clinical evaluation module 216 to assist with determining/measuring an effectiveness of treatment and/or assessing the potential need for surgery. The NIBP device 200 and/or monitoring can be used for out-patient and/or at-home patient monitoring to assist with monitoring the diabetic conditions, trends of the condition and/or evaluating the treatment therapy effectiveness. The blood delivery 224 monitoring can be controlled to occur, and/or increase monitoring, at required, and/or desired, times, such as during critical times and not occur, and/or decrease monitoring, during non-critical times.

An abdominal aortic aneurysm 226 can be identified and/or monitored by the clinical evaluation module 216. In an example, the NIBP module 201 can use ultrasound 202, which can also be used to image the aorta to assist with diagnosing and/or monitoring the aneurysm 226. Additionally, the vessel dynamics 223 can include measurements of the vessel which can also assist with identifying and/or monitoring the aneurysm 226. Further, local blood pressure 217 measurements can also assist with identifying and/or monitoring the aneurysm 226.

The clinical evaluation module 216 can also detect/identify the Return of Spontaneous Circulation (ROSC) 227 using the vessel dynamics 223 data. For example, the vessel dynamics 223 data can indicate blood flow, such as ROSC, which can be communicated to a user, device and/or system to assist with defibrillation shock administration decisions.

Internal bleeding 228 can also be identified, monitored and/or characterized using ultrasound 202. The ultrasound 202 can be used to detect internal bleeding 228 when placed over areas of the body where blood collects during internal bleeding 228. Further, the ultrasound 202 can be placed over trauma sites to identify the presence of ruptured vessels.

The clinical evaluation module 216 can also determine a heart rate 229 based on the NIBP, vital signs and/or other data, such as the vessel dynamics 223 data. The heart rate 229 can be displayed as a value and/or classification and can assist a user, device and/or system with patient monitoring and/or treatment.

The clinical evaluation module 216 can also provide cardiopulmonary resuscitation (CPR) feedback 230. The clinical evaluation module 216 can use NIBP data, such as from the NIBP module 201, and optionally vital signs data, such as from the vital signs module 208, to provide a measure of the efficacy of the applied CPR. For example, ventilation/oxygenation 209 data can be used to assess the efficacy of administered ventilations (both mechanically and manually administered) and can be measured by end tidal CO2 (etCO2) data. ECG 213 data and blood pressure data can be used to identify potential hemodynamic collapse and, optionally, generate an alert to a user. The vital signs data, such as ventilation/oxygenation 209 and/or ECG 213 data, and blood delivery 224 data can be quantified to provide a measurement of the efficacy of CPR being applied to a patient. A user, device and/or system can alter one or more characteristics of the CPR in response to the CPR feedback 230 provided by the NIBP device 200. For example, chest compression depth and/or rate and compression element position (i.e., hand position for manual CPR or piston position for mechanical CPR) can be altered in response to the CPR feedback 230. Further, the clinical evaluation module 216 can generate a user instruction or prompt to administer treatment to the patient based on the CPR feedback 230. The treatment can be continued CPR, defibrillation therapy, administration of medication, ventilation (mechanical and/or manual) or intubation procedures, etc.

Vascular blockage 231 can also be identified by the clinical evaluation module 216. The NIBP data can be evaluated to identify blockages, such as by ultrasound 202, and/or identify turbulent flow which can be indicative of blockages. The identification and/or monitoring of vascular blockage 231 can assist with monitoring and/or treatment of the patient.

The clinical evaluation module 216 can also monitor the NIBP, vital signs and/or other data for trends 232. The data can be aggregated over time to identify trends 232, which can assist with predicting a future physiological/clinical state/condition of the patient. The trending 232 data can be plotted, extrapolated and/or displayed to provide a user, device and/or system with data to assist with patient monitoring and/or treatment. Further, the extrapolation of the data can provide a prediction that one or more vital signs and/or conditions may potentially cross a threshold value, which can allow a user, device and/or system to take preventative, or proactive, action, such as patient treatment.

To assist with increasing the accuracy of the NIBP device 200, a user, device and/or system can provide various data. For example, the NIBP module 201 can use a fixed, or assumed, blood density in calculating the blood pressure of the patient. However, a patient can have a non-standard blood density, such as due to transfusions, infection, disease, or other factors, which can alter the overall density of the patient's blood. A user, device and/or system can provide an input to the NIBP device 200 that is indicative of the altered blood density to cause the NIBP device 200 to compensate for the altered blood density in calculating the blood pressure and/or vessel dynamics. Additionally, ultrasound contrast agents can be used to assist with the signal-to-noise ratio of detecting/monitoring the blood flow of the patient. The contrast agents can assist with increasing the accuracy and/or detectability of blood flow in areas of the patient's body in which it can otherwise be difficult to detect using ultrasound without contrast agents. Another method of increasing accuracy can include extending intervals of monitoring to reduce variations in the measurements that can be introduced due to noise. For example, the measurement data can be gathered over a period of time and averaged, and/or otherwise statistically manipulated, to improve the signal-to-noise ratio of the measured data.

Calibration can also be used to assist with increasing the accuracy of the NIBP device 200. For example, an automated or manual blood pressure measurement can be made and compared to the blood pressure measurement calculated by the NIBP device 200. The NIBP device 200 can then be calibrated and/or adjusted based on the automated or manual blood pressure measurement.

Calibration can also be implemented when using one or more NIBP devices 200 to measure blood pressure at multiple sites on the patient. For example, a reference NIBP calculation at a central location on the patient can be used to calibrate the NIBP calculation at a second location on the patient based on the separation and/or position of the central and second locations.

Figure 3:
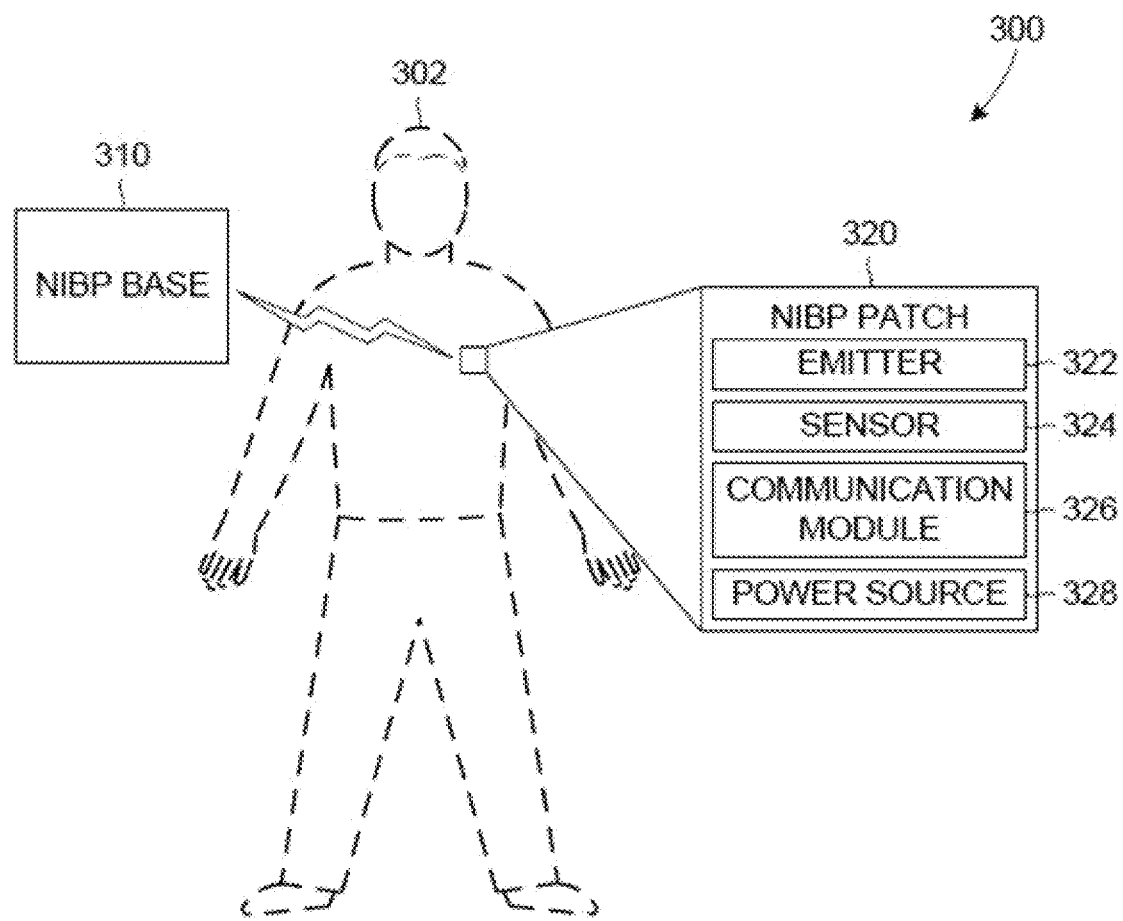
FIG. 3 is an example NIBP patch system.

FIG. 3 illustrates an example non-invasive blood pressure (NIBP) patch system 300 that includes an NIBP patch 320 that communicates with an NIBP base 310. The NIBP patch 320 is placed on a patient 302 and transmits an NIBP signal, or data, to the NIBP base 310. The NIBP base 310 can process the received NIBP signal to calculate a blood pressure and/or vessel dynamics of the patient 302.

The NIBP patch 320 can be releasably attached to the patient 302, such as by an adhesive, and can be worn by the patient for a period of time. In an example, a user can apply the NIBP patch 320 to the patient 302 to monitor the blood pressure, vessel dynamics and/or patient monitoring/treatment characteristics, with the NIBP base 310. In another example, the NIBP patch 320 can be applied to the patient 302 to collect patient data for an interval and/or spaced apart intervals, to collect various patient vital signs data over a period of time. The NIBP patch 320 can be disposable after a particular number of uses or type of use. For example, the NIBP patch could be disposable after being used a desired number of times on a single patient or on multiple patients. The NIBP patch is small in size and communicates wirelessly with its other system components, and, in some examples, it communicates with the processing circuitry that is physically located on another component with which the NIBP patch is configured to communicate wirelessly. In another example, the NIBP patch is used during a particular use, such as a surgery or a trauma event and is intended for a single use based on the type of application in which it is being used.

Alternatively, the NIBP device could be implanted into a patient as a permanent monitoring device at a specific site in the body. Because of its small size and wirelessly capabilities, the implantable NIBP device could communicate wirelessly with other system components and/or could be pro-grammed or re-programmed from a remote computing device to measure NIBP for certain conditions and under desired parameters. The implantable NIBP device could be powered by a battery or powered by radio waves, for example.

The NIBP patch 320 includes an emitter 322, a sensor 324, a communication module 326 and a power source 328. The emitter 322 can radiate energy, or waves, such as ultrasonic and/or light energy/waves, into the tissues of the patient 302. The radiated energy reflects from various tissues of the patient 302, such a flowing blood, and the sensor 324 receives the reflected energy. The reception of the reflected energy by the sensor 324 causes an NIBP signal, or data, to be generated.

Generally stated, the disclosed NIBP patch measures two values which can be used to compute a patient's instantaneous blood pressure. The NIBP patch measures the instantaneous non-invasive blood pressure (NIBP) of a patient with an apparatus that determines the values for, in one example, two of the unknowns in the water hammer equation: pulse wave velocity (PWV) and instantaneous blood velocity ($v_i$). The water hammer equation relates instantaneous blood pressure to pulse wave velocity and blood flow as follows:

$$P_i = \rho PWV v_i$$

where PWV is the pulse wave velocity, $\rho$ is the density of the blood which may be assumed to be a constant, for example, $v_i$ is the instantaneous velocity of the blood, and $P_i$ is the desired instantaneous blood pressure. Alternative equations relating the pulse wave velocity and blood flow can also be used.

Some conventional NIBP measurement systems rely on PWV to measure NIBP, but each requires an initial calibration measurement, taken at least once, to convert a relative blood pressure value to an actual blood pressure value. The required calibration measurement is typically taken using a traditional blood pressure cuff, for example on the patient's arm or perhaps the leg. Such conventional NIBP measurement systems that require an initial calibration and all calculations are based on a difference or differential value of that initial calibration measurement to achieve an actual measurement.

The disclosed NIBP systems and devices instead take an instantaneous blood pressure measurement rather than a change from an initial calibration measurement. Avoiding the need for a calibration measurement, prevents the patient from experiencing blood flow restriction altogether, which are required by all cuff-based NIBP systems. PWV is highly correlated with blood pressure (BP) so that changes in blood pressure can be calculated from changes in PWV by relying on an initial calibration measurement to produce a relatively accurate blood pressure measurement. The traditional calibration methods require use of a separate, initial calibration value or values to register a particular PWV to a particular value of blood pressure (as opposed to simply a change in blood pressure) for a patient. State of the art of NIBP using PWV typically uses a standard cuff-based measurement, to restrict the blood flow, in order to measure and associate a particular blood pressure to a particular PWV measurement in a patient. Restricting the blood flow requires that the patient's appendage being measured is compressed. Such restriction of the patient's blood flow prevents such conventional methods of measuring blood pressure from being applied to areas of the patient's body that cannot withstand restricted blood flow, such as a patient's neck, for example.

In this way, conventional methods and devices that provide NIBP measurements using PWV require a distinct calibration step. In contrast to the state of the art, the disclosed embodiments include a method and device that eliminate the requirement of a distinct calibration step, especially using a technology that temporarily restricts blood flow. In short, the disclosed embodiments include self-calibrating NIBP systems and methods using PWV, or alternatively, NIBP systems and methods using PWV without the temporary restriction of blood flow.

The lack of need for a calibration step for devices using the method taught herein arises from the use of the water hammer equation in its integrated (non-differential) form, for example. In the water hammer equation, the blood pressure is related to the PWV by two scale factors blood velocity and blood density that can be known without a distinct calibration step. The scale factors are found using the same ultrasound technology that is used to measure the PWV. Blood velocity is measured according to this disclosure and blood density is assumed based on a known value with or without a correction factor. In this way, a particular blood pressure is calculated as the PWV scaled by the blood density and the blood velocity.

Blood velocity can be acquired using ultrasound as a time varying waveform. PWV can also be measured with ultrasound as a time varying function. The time-varying nature of the PWV means that it can be updated from beat to beat or less frequently, if desired. The time-varying nature of the blood velocity means that blood velocity can be measured at a much finer resolution than at peak systole and diastole values during a cardiac cycle. Instead the blood velocity is measured continuously throughout the duration of the cardiac cycle for as many cardiac cycles as desired. Because blood density is already sufficiently known and is relatively constant, not only can a particular blood pressure measurement be known from the scaled value of the PWV as if it were obtained by a standard cuff-based measurement or even an invasive catheter measurement, but all manners of blood pressure measurements can be made as time-varying waveforms describing the instantaneous pressure at as many points during a cardiac cycle as desired. Blood pressure can be monitored continuously throughout the cardiac cycle with as fine a resolution as is required, and this can be done for as many consecutive or periodic cardiac cycles as is desired for beat-to-beat monitoring, or as intermittently as desired.

Measuring the instantaneous blood pressure instead of its change relative to a calibrated baseline measurement means, for example, that as arterial walls stiffen (due to disease, drug therapy, and/or normal vasculature responses, for example) which increases the PWV, this new PWV value is measured along with any corresponding change in blood velocity to produce an updated blood pressure waveform. Additionally, if the heart pumps more or less energetically, the blood velocity changes accordingly, which results in the blood pressure changing proportionately, all else equal. This updated blood velocity measurement at the prevailing PWV (which characterizes the state of the vasculature) corresponds to the updated blood pressure after being scaled by blood density. In other words, since there are two measurements made, PWV and blood velocity, and not just PWV alone, a distinct calibration step is not needed, as the ambiguity of PWV by itself is remedied by adding the second measured value of blood velocity. This is of great value over conventional patient NIBP monitoring using PWV alone where typically the calibration step requires a blood pressure measurement performed by restricting blood flow, which can be more costly, time consuming, and/or uncomfortable to the patient. Ultrasound or light technology can be used to acquire both the PWV and the blood velocity although other methods of obtaining the PWV and the blood velocity can alternatively or additionally be used. Further embodiments implement various techniques and devices to measure or detect both pulse wave velocity and instantaneous blood velocity.

An NIBP sensor can be attached to a patient, as shown in FIG. 3. As discussed at length above, the sensor includes an ultrasound sensor and may include one or more alternative sensors.

The NIBP sensor substantially simultaneously measures pulse wave velocity and instantaneous blood velocity, as discussed above. Each of those two basic steps may be accomplished in numerous ways. For example, pulse wave velocity may be measured using a sound analysis based on information known about the configuration of the NIBP sensor. In one specific embodiment, the sensor is configured such that an ultrasound waveform radiated by the sensor produces grating lobes having known characteristics, such as a grating lobe separation angle of θ. The sound analysis may further compute a depth from the sensor to a target blood vessel. Based on those data, ultrasound imaging combined with triangulation techniques can be used to compute a rate at which a pulse travels through the vessel, which is the pulse wave velocity of the vessel.

Similarly, instantaneous blood velocity may be measured using Doppler effect techniques. In one specific embodiment, the Doppler analysis can identify the phase change of a returned signal from the blood between each of 10 kHz repetitions, for example.

Once pulse wave velocity and instantaneous blood velocity are known, the instantaneous blood pressure is calculated by using an equation that relates the blood velocity to the PWV, such as the water hammer equation. Based on that equation, pulse wave velocity, instantaneous blood velocity, and blood pressure are related as follows:

$$P_i = \rho PWV v_i$$

Once calculated, the blood pressure measurement may be presented to a user for use in treatment of the patient. It should be appreciated that, in another alternative, continuous wave Doppler (CWD) may be used as an alternative to pulse wave Doppler (PWD).

Referring again to FIG. 3, the communication module 326 of the NIBP patch 320 can use one or more communication protocols, such as a network connection, to transmit data from the NIBP patch 320 to the NIBP base 310. In an example, the communication module 326 can communicate with the NIBP base 310 via a Bluetooth®, a near-field communication (NFC) connection, Wi-Fi Direct®, and/or WiGig. Data transmitted by the NIBP patch 320 to the NIBP base 310 can include the NIBP signal.

The power source 328 can include an energy storage device, such as a battery, and can supply the requisite energy to the various components/systems of the NIBP patch 320. The power source 328 can be permanently integrated with the NIBP patch 320, or can be removable/replaceable. Intermittent or modulated data collection by the NIBP patch 320 can extend the lifespan of the power source 328, allowing data to be collected over a period of time.

Figure 4A:
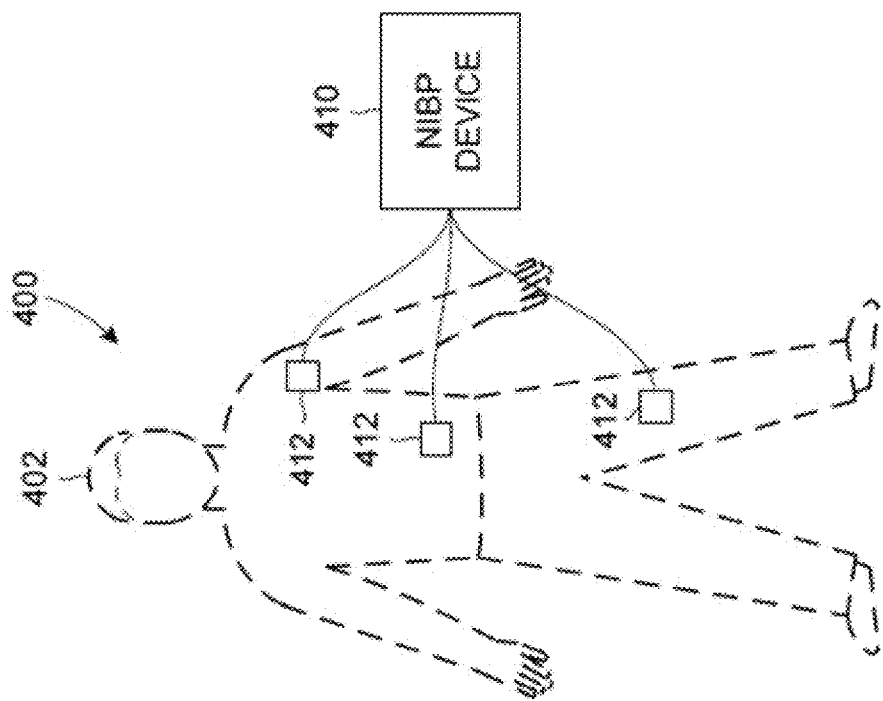
FIGS. 4A-4B are example NIBP monitoring systems.
Figure 4B:
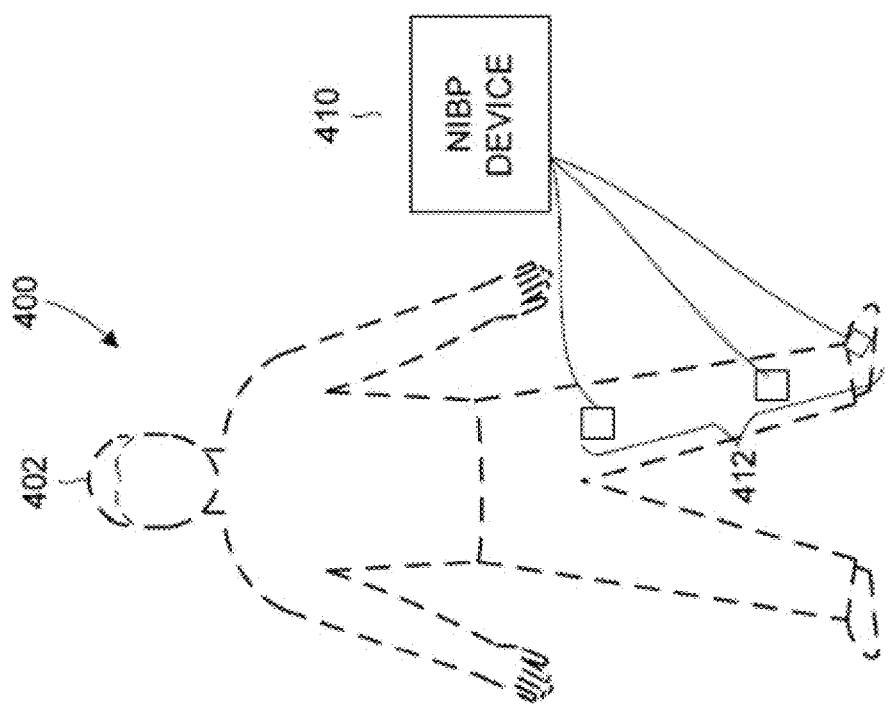

FIGS. 4A-4B illustrate example multi-site NIBP monitoring systems 400 that include an NIBP device 410 and NIBP sensors 412. The NIBP sensors 412 can be placed on a patient 402 to generate NIBP signals/data that can be processed by the NIBP device 410 to calculate a blood pressure and/or vessel dynamics of the patient 402. Multi-site blood pressure monitoring can include two or more NIBP sensors 412 that can be distributed and/or placed at various positions on the body of the patient 402. In FIG. 4A, the NIBP sensors 412 are dispersed across the body of the patient 402 for whole body blood pressure monitoring. In FIG. 4B, the NIBP sensors 412 are clustered or strategically placed around an area for local blood pressure monitoring, such as might be used in a surgery situation. The example shown in FIG. 4B could be used to monitor a diabetes patient for blood flow, blood pressure, and/or vessel dynamics in/through the patient's leg to improve the efficacy of diabetes treatment in the patient in both an emergency and nonemergency setting. Further, alternative arrangements could cluster multiple NIBP patches around a pregnant women's abdomen to measure blood pressure, blood flow, and/or vessel dynamics of the mother and fetus during pregnancy. Other example configurations are included and can be patient-specific and/or disease/infection/operating environment-specific, as needed.

Figure 5:
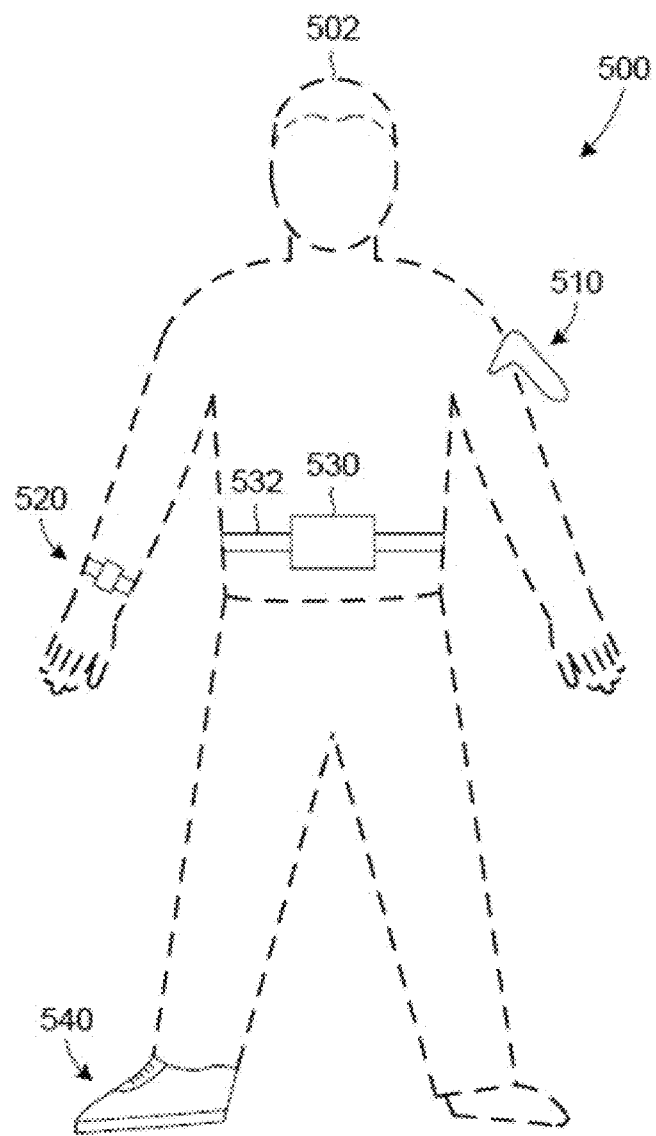
FIG. 5 is an example wearable and/or contactable NIBP system.

FIG. 5 illustrates an example wearable and/or contactable NIBP system 500. The system 500 includes a wearable and/or contactable NIBP device that can be placed on a patient 502 to monitor a blood pressure and/or vessel dynamics of the patient 502. Contactable NIBP devices can be placed against the skin of the patient 502 and wearable articles can secure the contactable NIBP devices so they are worn by the patient 502, such as for an extended period of time.

An example contactable device can include a handheld NIBP device 510 that a user, or other, can press against the skin of the patient 502 to calculate a blood pressure and/or vessel dynamics. The handheld NIBP device 510 can be held against the patient's skin to acquire the NIBP signal and/or data and can provide a notification to the user when such data has been collected and/or processed.

Example wearable articles with a NIBP device can include a watch 520, an NIBP device 530 on a belt 532, a shoe 540 and/or other wearable articles like vests and/or harnesses. In the example watch 520 and shoe 540, the NIBP device can be integrated into the wearable item and can include an NIBP sensor that contacts the skin of the patient 502 to generate the NIBP signal and/or data. The NIBP device 530 on a belt 532 can include a sensor that contacts the patient 502 to generate the NIBP signal and/or data. The wearable devices can be worn for extended period of times to monitor the blood pressure and/or vessel dynamics of the patient 502. The collected monitoring data can assist with patient 502 care and/or treatment. The NIBP devices 520, 530, 540 could be removable from their respective wearable article that then secures the NIBP device for contact against the patient.

Figure 6:
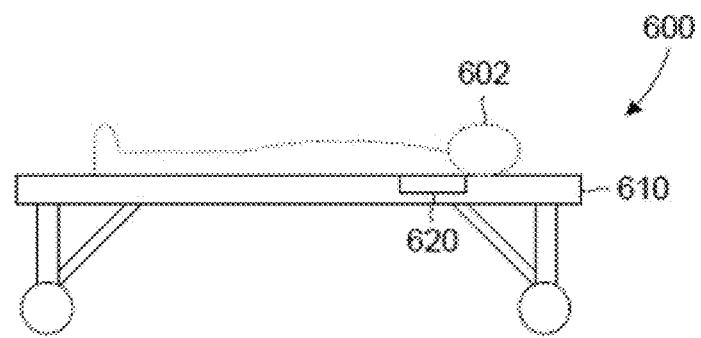
FIG. 6 is a further example contactable NIBP system.

FIG. 6 illustrates another contactable NIBP system 600 that includes an NIBP device 620 that is integrated with and/or placed in a patient bed/gurney 610. The NIBP device 620 includes a sensor that contacts a patient 602 that is lying in the patient bed 610, such as a hospital bed, gurney, cot, or other patient transport device. The sensor can generate an NIBP signal and/or data that can be processed to calculate a blood pressure and/or vessel dynamics of the patient 602. The contactable NIBP device 620 can be integrated in other objects and/or items that a patient 602 can come into contact with, such as patient injury support devices and/or other support structures. The integration of a contactable NIBP device can assist with monitoring and/or treating a patient based on the data collected and/or calculated by the NIBP device.

Figure 7:
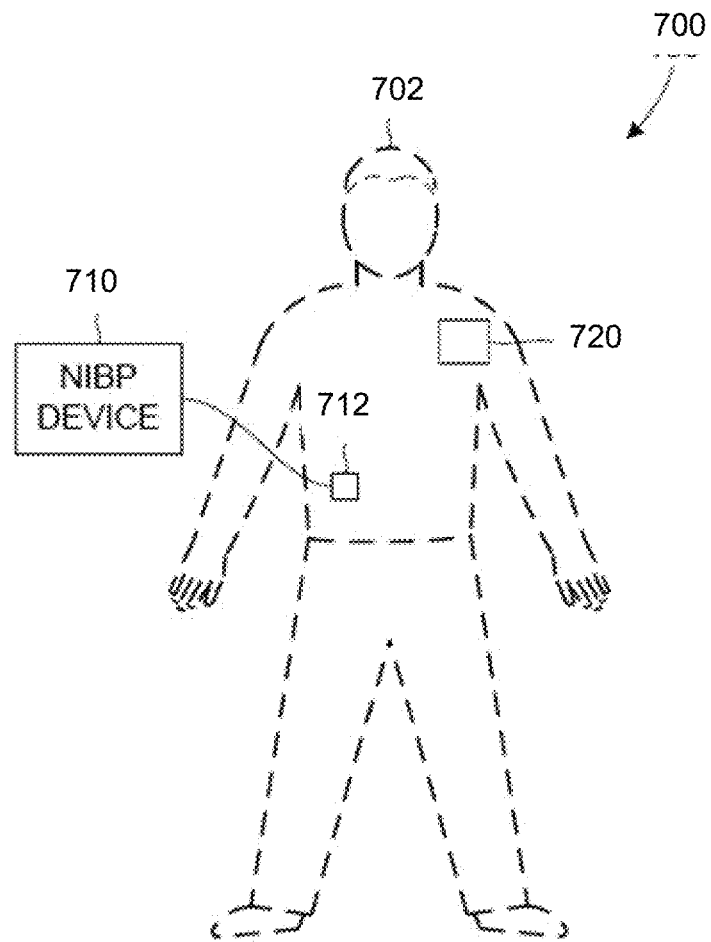
FIG. 7 is an example non-invasive blood pressure (NIBP) system.

FIG. 7 illustrates an example non-invasive blood pressure (NIBP) system 700. The NIBP system 700 can include an NIBP device 710 and an NIBP sensor 712 and/or an NIBP patch 720, which can be placed on a patient 702. The NIBP device 710 and sensor 712 and/or the NIBP patch 720 can determine a blood pressure and/or vessel dynamics, such as blood flow, size and/or position of a vessel, of the patient 702.

To calculate, or determine, the blood pressure and/or vessel dynamics of the patient 702, the NIBP sensor 712 and/or the NIBP patch 720 can radiate energy, such as ultrasound and/or light, into the tissues of the patient 702. The radiated energy will reflect from the various tissues, such as vessels, flowing blood, and/or other tissues/features, and the reflected energy can be sensed by the NIBP sensor 712 and/or the NIBP patch 720 to generate an NIBP signal, or data. The NIBP signal can be processed, such as by the NIBP device 710 and/or NIBP patch 720, to calculate a blood pressure and/or vessel dynamics of the patient 702.

Generally stated, the disclosed NIBP patch measures two values which can be used to compute a patient's instantaneous blood pressure. The NIBP patch measures the instantaneous non-invasive blood pressure (NIBP) of a patient with an apparatus that determines the values for, in one example, two of the unknowns in the water hammer equation: pulse wave velocity (PWV) and instantaneous blood velocity ($v_i$). The water hammer equation relates instantaneous blood pressure to pulse wave velocity and blood flow as follows:

$$P_i = \rho PWV v_i$$

where PWV is the pulse wave velocity, $\rho$ is the density of the blood which may be assumed to be a constant, for example, $v_i$ is the instantaneous velocity of the blood, and $P_i$ is the desired instantaneous blood pressure. Alternative equations relating the pulse wave velocity and blood flow can also be used.

Some conventional NIBP measurement systems rely on PWV to measure NIBP, but each requires an initial calibration measurement, taken at least once, to convert a relative blood pressure value to an actual blood pressure value. The required calibration measurement is typically taken using a traditional blood pressure cuff, for example on the patient's arm or perhaps the leg. Such conventional NIBP measurement systems that require an initial calibration and all calculations are based on a difference or differential value of that initial calibration measurement to achieve an actual measurement.

The disclosed NIBP systems and devices instead take an instantaneous blood pressure measurement rather than a change from an initial calibration measurement. Avoiding the need for a calibration measurement, prevents the patient from experiencing blood flow restriction altogether, which are required by all cuff-based NIBP systems. Although PWV is highly correlated with blood pressure (BP) so that changes in blood pressure can be calculated from changes in PWV by relying on an initial calibration measurement relatively accurately, the traditional calibration methods require use of a separate, initial calibration value or values to register a particular PWV to a particular value of blood pressure (as opposed to simply a change in blood pressure) for a patient. State of the art of NIBP using PWV typically uses a standard cuff-based measurement, to restrict the blood flow, in order to measure and associate a particular blood pressure to a particular PWV measurement in a patient. Restricting the blood flow requires that the patient's appendage being measured is compressed. Such restriction of the patient's blood flow prevents such conventional methods of measuring blood pressure from being applied to areas of the patient's body that cannot withstand restricted blood flow, such as a patient's neck, for example.

In this way, conventional methods and devices that provide NIBP measurements using PWV require a distinct calibration step. In contrast to the state of the art, the disclosed embodiments include a method and device that eliminate the requirement of a distinct calibration step, especially using a technology that temporarily restricts blood flow. In short, the disclosed embodiments include self-calibrating NIBP systems and methods using PWV, or alternatively, NIBP systems and methods using PWV without the temporary restriction of blood flow.

The lack of need for a calibration step for devices using the method taught herein arises by making an additional measurement of the vasculature such as blood velocity and a suitable equation such as the water hammer equation in its integrated (non-differential) form. In the water hammer equation, the blood pressure is related to the PWV by two scale factors—blood velocity and blood density—that can be known without a distinct calibration step. The scale factors are found using the same ultrasound technology that is used to measure the PWV. Blood velocity is measured according to the disclosure and blood density is assumed based on a known value with or without a correction factor. In this way, a particular blood pressure is calculated as the PWV scaled by the blood density and the blood velocity.

Blood velocity can be acquired using ultrasound as a time varying waveform. PWV can also be measured with ultrasound as a time varying function. The time-varying nature of the PWV means that it can be updated from beat to beat, if desired. The time-varying nature of the blood velocity means that blood velocity can be measured at a much finer resolution than at peak systole and diastole values during a cardiac cycle. Instead, the blood velocity is measured continuously throughout the duration of the cardiac cycle for as many cardiac cycles as desired. Because blood density is already sufficiently known and is relatively constant, not only can a particular blood pressure measurement be known from the scaling value of the PWV as if it were obtained by a standard cuff-based measurement or even an invasive catheter measurement, but all manners of blood pressure measurements can be made as time-varying waveforms describing the instantaneous pressure at as many points during a cardiac cycle as desired. Blood pressure can be monitored continuously throughout the cardiac cycle with as fine a resolution as is required, and this can be done for as many consecutive or periodic cardiac cycles as is desired for beat-to-beat monitoring, or as intermittently as desired.

Measuring the instantaneous blood pressure instead of its change relative to a calibrated baseline measurement means, for example, that as arterial walls stiffen (due to disease, drug therapy, and/or normal vasculature responses, for example) which increases the PWV, this new PWV value is measured along with any corresponding change in blood velocity to produce an updated blood pressure waveform. Additionally, if the heart pumps more or less energetically, the blood velocity changes accordingly, which results in the blood pressure changing proportionately, all else equal. This updated blood velocity measurement at the prevailing PWV (which characterizes the state of the vasculature) corresponds to the updated blood pressure after being scaled by blood density. In other words, since there are two measurements made, PWV and blood velocity, and not just PWV alone, a distinct calibration step is not needed, as the ambiguity of PWV by itself is remedied by adding the second measured value of blood velocity. This is of great value over conventional patient NIBP monitoring using PWV alone where typically the calibration step requires a blood pressure measurement performed by restricting blood flow, which can be more costly, time consuming, and/or uncomfortable to the patient. Ultrasound or light technology can be used to acquire both the PWV and the blood velocity although other methods of obtaining the PWV and the blood velocity can alternatively or additionally be used. Further embodiments implement various techniques and devices to measure or detect both pulse wave velocity and instantaneous blood velocity.

An NIBP sensor can be attached to a patient. As discussed at length above, the sensor includes an ultrasound sensor and may include one or more alternative sensors.

The NIBP sensor substantially simultaneously measures pulse wave velocity and instantaneous blood velocity, as discussed above. Each of those two basic steps may be accomplished in numerous ways. For example, pulse wave velocity may be measured using a sound analysis based on information known about the configuration of the NIBP sensor. In one specific embodiment, the sensor is configured such that an ultrasound waveform radiated by the sensor produces grating lobes having known characteristics, such as a grating lobe separation angle of θ. The sound analysis may further compute a depth from the sensor to a target blood vessel. Based on those data, ultrasound imaging combined with triangulation techniques can be used to compute a rate at which a pulse travels through the vessel, which is the pulse wave velocity of the vessel.

Similarly, instantaneous blood velocity may be measured using Doppler effect techniques. In one specific embodiment, the Doppler analysis can identify the phase change of a returned signal from the blood between each of 10 kHz repetitions, for example.

Once pulse wave velocity and instantaneous blood velocity are known, the instantaneous blood pressure is calculated by using an equation that relates the blood velocity to the PWV, such as the water hammer equation. Based on that equation, pulse wave velocity, instantaneous blood velocity, and blood pressure are related as follows:

$$P_i = \rho PWV v_i$$

Once calculated, the blood pressure measurement may be presented to a user for use in treatment of the patient. It should be appreciated that, in another alternative, continuous wave Doppler (CWD) may be used as an alternative to pulse wave Doppler (PWD).

The calculated blood pressure and/or vessel dynamics of the patient 702 can assist with monitoring and/or treating the patient 702. For example, the blood pressure and/or vessel dynamics data can be collected over an extended period of time to assist with monitoring the patient 702 and/or the efficacy of patient 702 treatment can be assessed based on the calculated blood pressure and/or vessel dynamics. Using such data, a user, device and/or system can alter treatment of the patient 702 to increase the efficacy of the administered treatment, such as cardiopulmonary resuscitation (CPR).

Data from the NIBP sensor 712, such as the NIBP signal/data, can be transmitted to the NIBP device 710 for processing. Communications between the NIBP device 710 and the NIBP sensor 712 can be via a wired and/or a wireless connection. In addition to communication, the connection between the NIBP device 710 and the NIBP sensor 712 can provide power from one or more of the NIBP device 710 and/or the NIBP sensor 712 to the other. The NIBP device 710 can display and/or transmit the blood pressure and/or vessel dynamics data to a user, device and/or system.

The NIBP patch 720 can be placed on and/or affixed to the skin of the patient 702, such as by an adhesive backing. With the NIBP patch 720 placed on and/or affixed to the patient 702, the NIBP patch 720 can calculate/monitor the blood pressure and/or vessel dynamics of the patient 702 in a continuous and/or interval manner. The NIBP patch 720 can remain on and/or affixed to the patient 702 for extended period times to allow the NIBP patch 720 to capture blood pressure and/or vessel dynamic data over the extended period of time.

Data, such as blood pressure and/or vessel dynamics, can be transmitted from the NIBP patch 720 to an external device and/or system. Such communication can be via a wired and/or a wireless connection, such as via a near-field communication (NFC), Wi-Fi Direct®, WiGig, cellular, and/or Bluetooth® connection. Additionally, or alternatively, the blood pressure and/or vessel dynamics data can be stored on the NIBP patch 720 for later retrieval.

Figure 8:
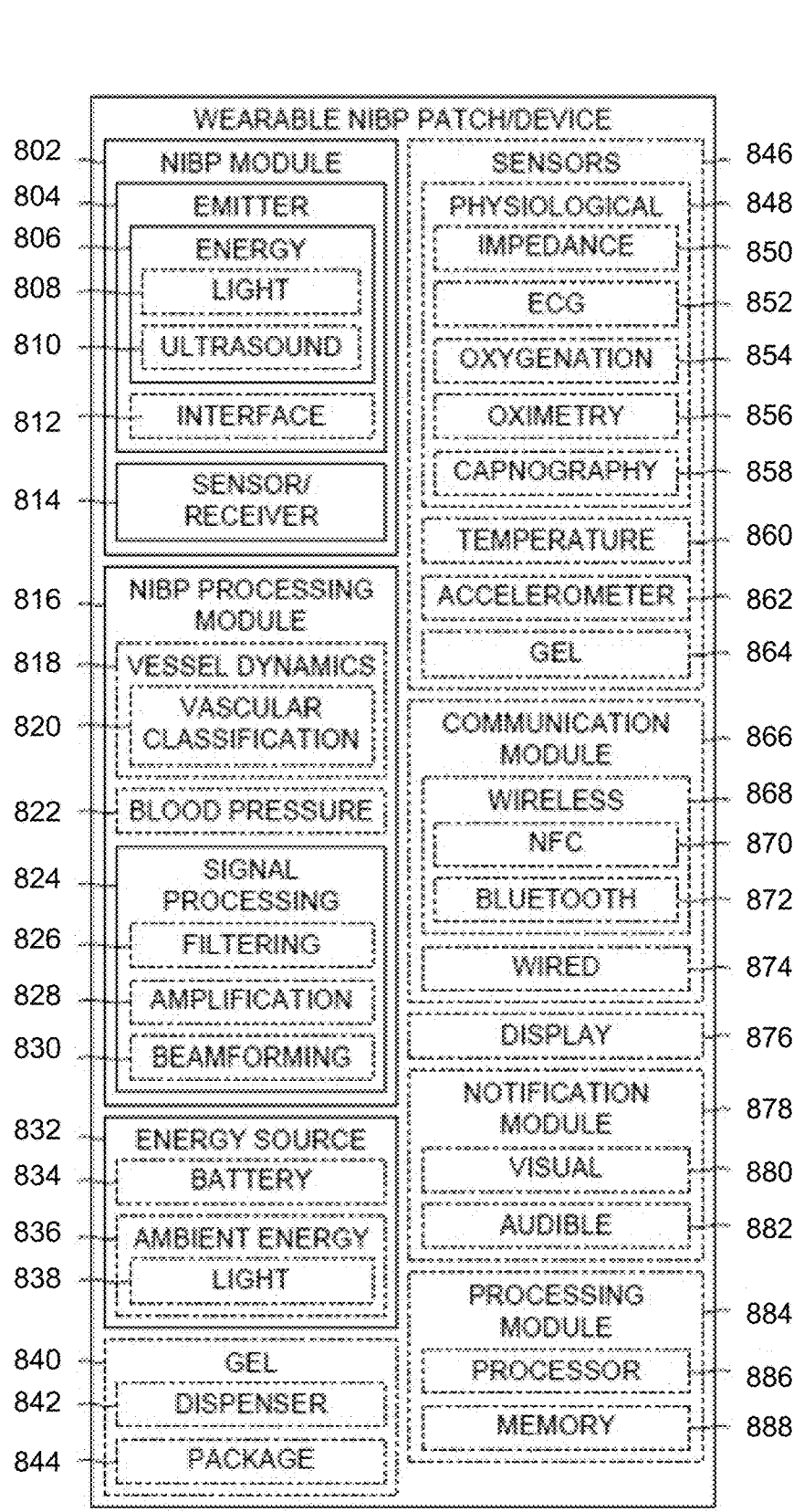
FIG. 8 is a block diagram of an example wearable NIBP patch or device.

FIG. 8 illustrates an example non-invasive blood pressure (NIBP) patch/wearable device 800 that can be placed on, or affixed to, a patient to determine/calculate a blood pressure and/or vessel dynamics of the patient. The NIBP patch/wearable device 800 can include various elements/systems, features and/or functionality that can be contained in/on the NIBP patch/wearable device 800. Example elements/systems, features and/or functionality of the NIBP patch/wearable device 800 can include an NIBP module 802, an NIBP processing module 816, an energy source 832, gel 840, sensor(s) 846, a communication module 866, a display 876, a notification module 878 and/or a processing module 884. Alternatively, one or more elements/systems, features and/or functionality of the NIBP patch/wearable device 800 can be distributed on, and/or integrated with, an external device/system.

The NIBP module 802 can include an emitter 804 and a sensor/receiver 814. The emitter 804 can radiate energy 806, such as light 808 and/or ultrasound 810, into tissues of a patient and the sensor/receiver 814 can receive energy reflected from the tissues of the patient. Reception of the reflected energy can cause the sensor/receiver 814 to generate an NIBP signal/data that can be processed to calculate a blood pressure and/or vessel dynamics of the patient.

An optional interface 812 of emitter 804 can assist with directing energy 806 of the emitter 804 into the patient's tissues. For ultrasound energy 810 radiation, the interface 812 can be textured with microstructures that can abrade the outer skin of the patient such that the microstructures of the interface 812 are acoustically integrated with the outer skin of the patient. This integration of the interface 812 and the patient's skin can direct the ultrasound energy 810 into the tissues of the patient without requiring the use of a gel.

The NIBP processing module 816 can receive the NIBP signal and/or data from the NIBP module 802 for processing 824 to calculate vessel dynamics 818 and/or blood pressure 822 of the patient. Processing 824 of the NIBP signal/data can include analog filtering 826, amplification 828 and/or beamforming 830. Beamforming 830 can be applied to, and/or implemented with, the ultrasound 810 emissions by the emitter 804 to assist with enhancing the ultrasound signal(s)/data captured by the sensor/receiver 814. The beamforming 830 can include controlling, or altering, the emission of the ultrasonic 810 emissions by the emitter 804, such as altering a phase and/or amplitude of the output ultrasonic energy 810.

Calculating vessel dynamics 818 can include calculating/determining a depth of a vessel, a cross-sectional area of the vessel, a flow rate through the vessel and/or other dynamics/characteristics of one or more vessels based on the NIBP signal/data. Based on the vessel dynamics 818, the NIBP processing module 816 can also classify 820 one or more of the vessels interrogated by the NIBP module 802. The vascular classification 820 can include classifying the one or more vessels as a vein or artery, such as based on a calculated flow velocity and/or pressure within the one or more vessels.

The on-board energy source 832 can provide power, such as electrical power, to the various elements, features and/or functions of the wearable NIBP patch/device 800. An example on-board energy source 832 can include a battery 834 and/or an ambient energy 836 capture/storage element, device, and/or system. The battery 834 can be a permanent or replaceable battery that can be placed on/in, or affixed to, the wearable NIBP patch/device 800. The ambient energy 836 capture/storage can harvest ambient energy from about the wearable NIBP patch/device 800, such as from light 838, heat, movement and/or radio transmissions/waves. The ambient energy 836 capture/storage can receive, or be exposed to, the ambient energy and can convert the received ambient into electrical energy that can be stored, such as in the battery 834. The ambient energy 836 capture can include a solar/photovoltaic cell, a thermoelectric element, a piezoelectric material, a generator, a magnet in motion relative to a coil, and/or an antenna, to harvest/capture ambient energy.

Prior to use, the energy source 832 can be isolated, such as by a removable material, from connecting to the NIBP patch/device 800 circuitry, elements, and/or systems. This isolation can assist with reducing, or minimizing, depletion of the energy source 832 when the NIBP patch/device 800 is not in use, such as during storage prior to use. To activate and/or prepare the NIBP patch/device 800 for use, a user can remove the isolation material, such as via a pull tab, to allow/electrically connect the energy source 832 to the circuitry of the NIBP patch/device 800.

Gel 840 can be included on and/or in the wearable NIBP patch/device 800 as a dispenser 842 and/or a package 844. The gel 840 can interface between the skin of the patient and an ultrasound 810 emitter 804 to assist with directing the ultrasound energy 810 into the tissues of the patient. The gel 840 can prevent an air space/separation between the skin of the patient and the emitter 804 to prevent the reflection of the ultrasound energy 810 from the surface of the patient's skin.

The dispenser 842 of gel 840 can be an element, device and/or system that can dispense the gel 840 below the emitter 804 prior to and/or during use of the emitter 804 and/or wearable NIBP patch/device 800. In an example, the wearable NIBP patch/device 800 can be worn for an extended period of time and during the time the NIBP patch/device 800 is worn by the patient, the dispenser 842 can dispense gel 840 continuously, at intervals, and/or as needed, for example by evaluating the image generated. The dispenser 842 can maintain a gel 840 interface between the patient's skin and the emitter 804 while the wearable patch/device 800 is affixed and/or collecting data.

The package 844 of gel 840 can be a self-contained package 844 of gel 840 that can be broken prior to, or as/due to, the wearable NIBP patch/device 800 is being affixed/attached to, and/or placed on, the skin of a patient. The package 844 can be positioned such that the gel 840 is deposited on and/or below the emitter 804 such that a gel 840 interface between the emitter 804 and the patient's skin is formed. In a disposable wearable NIBP patch/device 800, the package 844 of gel 840 can be affixed to the wearable NIBP patch/device 800. In an example, the package 844 of gel 840 can be integrated with the energy source 832 isolator, such that removal of the isolator causes the package 844 to break and dispense gel 840 and/or causes the package 844 to be exposed in a manner to allow breakage of the package 844 and the dispensing of gel 840 therefrom. In a non-disposable wearable NIBP patch/device 800, the package 844 of gel 840 can be manually placed, and/or broken, beneath the wearable NIBP patch/device 800 to form the gel 840 interface. Alternatively, gel 840 can be manually placed beneath the wearable NIBP patch/device 800 prior to attaching/placing the wearable NIBP patch/device 800 on the patient's skin.

The sensor(s) 846 of the wearable NIBP patch/device 800 can include a physiological sensor 848, a temperature sensor 860, an accelerometer 862, a gel sensor 864 and/or other sensors. The sensor(s) 846 can be placed on/in the wearable NIBP patch/device 800 to collect various sensor data of the patient, wearable NIBP patch/device 800, the ambient environment and/or other data. Alternatively, the sensor(s) 846 can be external to the wearable NIBP patch/device 800 and can communicate the sensed data via a wired and/or a wireless connection to the wearable NIBP patch/device 800. The data collected by the sensor(s) 846 can be transmitted from the wearable NIBP patch/device 800 to an external user, device and/or system and/or the data can be used with/in one or more functions and/or features of the wearable NIBP patch/device 800.

The wearable NIBP patch/device can include biocompatible materials, especially when intended for long-term contact with the patient's body. For example, the adhesive used to affix the NIBP patch/device to the patient could include similar adhesives found in conventional bandages and the patch material itself could also borrow from biocompatible materials used in typical bandages such as medical grade fabrics to avoid skin irritation. The gel used to wet the interface between an ultrasound NIBP patch/device and the patient's skin would also need to be biocompatible as would the sensor interface that contacts the patient's skin in the NIBP patch/device using any energy source (e.g., ultrasound and/or light). Still further, the ultrasound NIBP patch/device example would also include a biocompatible scan head lens(es), such as RTV, Rexolite, and/or some polyurethanes.

The physiological sensor(s) 848 can include an impedance sensor 850, an electrocardiogram (ECG) sensor 852, an oxygenation sensor 854, an oximetry sensor 856, a capnography sensor 858 and/or other physiological sensor 848. The collected physiological parameter data from the physiological sensor(s) 848 can be used by the wearable NIBP patch/device 800 to assist with monitoring and/or treatment of the patient to which the NIBP patch/device 800 is placed and/or affixed. Data from the sensor(s) 848 can be collected in a continuous and/or interval manner and can also be triggered by one or more events, such as a sensed value by the sensor(s) 846, a time and/or other trigger. Additionally, the physiological parameter data can be merged/processed with the blood pressure 822 and/or vessel dynamics 818 data to assist with monitoring and/or treatment of the patient. The merging/processing of such data can be performed on the wearable NIBP patch/device 800, such as by the processing module 884 and/or the NIBP processing module 816, and/or can be performed at/on an external device/system.

The temperature sensor 860 can monitor a temperature of the wearable NIBP patch/device 800 and/or the skin of the patient. In an example, the temperature sensor 860 can cause a performance parameter of the NIBP patch/device 800, such as a duty-cycle or sampling rate, of the wearable NIBP patch/device 800 to be decreased when a sensed temperature exceeds a threshold value which can prevent thermal damage to the patient's skin and/or patient discomfort while wearing the NIBP patch/device 800. Alternatively, or additionally, the temperature sensor 860 can cause one or more elements, devices and/or systems of the NIBP patch/device 800 to be disabled, such as temporarily, in response to a sensed temperature exceeding a value. Once the temperature sensor 860 senses that the temperature of the NIBP patch/device 800 and/or the patient's skin has decreased below a threshold, or other, value, the temperature sensor 860 can cause the NIBP patch/device 800 to resume normal, or prior, functioning.

The accelerometer 862 can sense motion of the NIBP patch/device 800. The accelerometer 862 can the NIBP patch/device 800 to monitor the motion, posture, position, acceleration and/or other motion parameters of the patient wearing the NIBP patch/device 800. In an example, the accelerometer 862 can trigger an alert/notification in response to one or more values, such as those that can indicate a collapse of the patient wearing the NIBP patch/device 800. Additionally, the accelerometer 862 can cause the acquisition of data, such as by the NIBP module 802 and/or sensors 846 in response to one or more values. In the example of a patient collapse, the NIBP module 802 can be triggered to acquire a blood pressure 822 and/or vessel dynamics 818 data to determine if the collapse was caused by, and/or caused, a physiological change of the patient.

Further, the accelerometer 862 can be integrated with another sensor, such as global positioning (GPS), and/or other geolocation, sensor which can determine a location of the patient wearing the NIBP patch/device 800. The location of the patient can be transmitted, such as by the communication module 866, to an external user, device and/or system in response to an accelerometer 862 value and/or change in value, such as caused by a collapse of the patient. Other data, such as sensor(s) 846 and/or NIBP module 802 data, can be transmitted along with the location of the patient.

The gel sensor 864 can monitor the integrity of the gel 840, such as a hydration of the gel 840. In extended period of wearing of the NIBP patch/device 800, the integrity of the gel 840 interface can deteriorate. The gel sensor 864 can monitor the integrity of the gel 840 interface and can trigger an alert, such as to apply more/new gel 840, and/or cause a dispenser 842 to dispense more gel 840 to the interface.

The communication module 866 can provide wired 874 and/or wireless 868 communications from and/or to the NIBP patch/device 800. The wireless communication 868 can be via a network, such as a Wi-Fi connection, Wi-Fi Direct, WiGig, cellular and/or can be a local connection, such as via near-field communication (NFC) 870 and/or Bluetooth® connection. Additionally, the NFC connection 870 can receive radio transmissions that can be converted to electrical power to provide power to one or more functions of the NIBP patch/device 800. Data transmission to and/or from the NIBP patch/device 800 can be with an external user, device and/or system and can include the various physiological data, such as sensor(s) 846 data and/or NIBP module 802 data, and/or instructions to cause the NIBP patch/device 800 and/or an external device/system to perform one or more functions.

Functioning/status of the NIBP patch/device 800 can also be obtained via the communication module 866. The NIBP patch/device 800 can be interrogated, such as via the NFC 870 and/or Bluetooth® 872 connection, for a status of the NIBP patch/device 800 and/or the status various elements, devices, systems and/or functionality thereof. As part of the interrogation, the NIBP patch/device 800 can also transmit identifying information, such as a serial number of the NIBP patch/device 800. Status of the NIBP patch/device 800 can include self-test data, a status of the gel 840 as sensed/determined by the gel sensor 864, an activation date of the NIBP patch/device 800, and/or other NIBP patch/device 800 status information. In an example, the status of the NIBP patch/device 800 can include a status of the energy source 832, remaining energy, remaining NIBP patch/device 800 run time on the available energy, and/or other status information regarding the energy source 832.

If the status of the NIBP patch/device 800 indicates a depleted and/or low power of the energy source 832, a user or other can replace the energy source 832 and/or replace the NIBP patch/device 800 with a new NIBP patch/device 800. As part of replacement of the NIBP patch/device 800, data from each NIBP patch/device 800 can be collected prior to removal of the old/depleted NIBP patch/device 800 to allow the measurements, such as blood pressure 822, to be compared for correlation. The correlation of the data can be used to verify that the data from each of the NIBP patches/devices 800 is correct, or agreed upon, between the two NIBP patches/devices 800. Alternatively, or additionally, the data collected from one or more of the NIBP patches/devices 800 can be corrected to align the data collected from both NIBP patches/devices 800.

An optional display 876 can provide a visual output to the user and/or others, such as to display the NIBP module 802, sensor(s) 846 and/or other data. The display 876 can include a screen upon which such data can be displayed and/or one or more other types of output to a user such as audible, visual, haptic, and/or other output. Additionally, the display 876 can provide input functionality, such as a touchscreen, to allow a user, or other, to input instructions and/or data to the NIBP patch/device 800.

The notification module 878 can provide visual 880 and/or audible 882 notifications, such as alerts, to the patient, a user, a device and/or system. Other types of notifications, such as haptic output, can also be used and any combination of the disclosed notifications can also be included. The notifications can be in response to sensed data, such as the blood pressure 822, vessel dynamics 818, sensor(s) 846 and/or other data. Additionally, and/or alternatively, the notifications can be with regards to one or more elements, devices and/or systems of the NIBP patch/device 800 and/or functioning thereof. For example, the notification module 878 can provide a notification when the energy source 832 is low so that a user can take appropriate action to continue the functioning of the NIBP patch/device 800, if desired/required.

When the energy source 832 is low, the user can be alerted to measure the battery consumption with a coulomb counter or alternatively an energy consumption estimator, for example. If blood pressure is still needed when the NIBP patch energy source is nearly drained, the user is alerted by the monitoring device. The user is prompted to place a new patch in place of or near the depleted one and measurements may be initially compared, in some examples, between the two NIBP patches before the near-depleted one is removed, and logged for any retrospective questions regarding differences in device or location on the body.

The processing module 884 can process data and/or control one or more functions/features of the NIBP patch/device 800. The processing module 884 can include a processor 886 and/or memory 888 for storing data and/or instructions for execution by the processor 886. Data stored in the memory 888 can include blood pressure 822, vessel dynamics 818, sensor(s) 846 and/or other data of the NIBP patch/device 800. The processing module 884 can monitor/process data from the sensor(s) 846 and/or the NIBP module 802 and can cause one or more function/features of the NIBP patch/device 800 to be performed in response to the data. Additionally, the processing module 884 can receive data and/or instructions from an external device/system, such as via the communication module 866, and can cause one or more function/features of the NIBP patch/device 800 to be performed in response.

The processing module 884 can also control the acquisition of data, such an NIBP signal/data and/or sensor(s) 846 data, by the NIBP patch/device 800. The processing module 884 can schedule the data acquisition, such as a continuous, interval and/or spaced apart data acquisition(s). Further, the acquisition of data via the NIBP module 802, NIBP processing module 816 and/or the sensor(s) 846 can be combined or interleaved, such as based on a desired, or required, sampling rate, for the one or more data acquisitions. Alternatively, the acquisition of the NIBP data and/or sensor data can be asynchoronously combined. Additionally, the acquisition of data by the NIBP patch/device 800 can be performed on an instructed basis, such as in response to receiving an external communication via the communication module 866 to cause one or more of a blood pressure 822, vessel dynamics 818, and/or sensor(s) 846 data.

Figure 9:
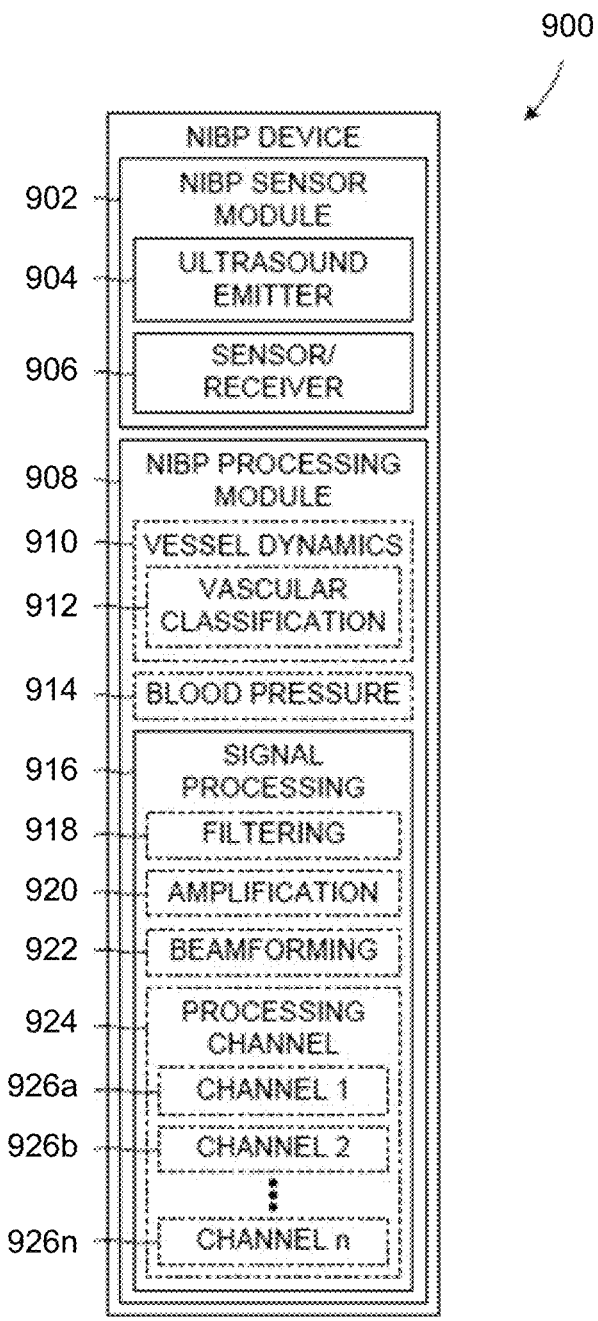
FIG. 9 is a block diagram of an example NIBP device.

FIG. 9 illustrates an example non-invasive blood pressure (NIBP) device 900 that can calculate, or determine, one or more vessel dynamics 910 and/or blood pressure 914 of a patient that the NIBP device 900 monitors, as discussed above. The NIBP device 900 includes an NIBP sensor module 902 and an NIBP processing module 908. The NIBP sensor module 902 can radiate energy into tissues of the patient and can sense, or receive, energy reflected therefrom to generate an NIBP signal and/or data. The NIBP processing module can process the NIBP signal/data to calculate the blood pressure 914 and/or vessel dynamics 910 of the patient.

The NIBP sensor module 902 can include an ultrasound emitter 904 and a sensor/receiver 906. The ultrasound emitter 904 radiates ultrasound waves into the tissues of the patient and the reflected energy can be sensed by the sensor/receiver 906 to generate the NIBP signal/data.

The NIBP processing module 908 can include signal processing 916 to calculate the blood pressure 914 and/or vessel dynamics 910 of the patient based on the NIBP signal and/or data from the NIBP sensor module 902. The signal processing 916 can include filtering 918, amplification 920 and/or beamforming 922. The NIBP signal/data can be received at the NIBP processing module 908 via various processing channels 924, such as channel 926a, 926b . . . 926n. The number of processing channels 924 can be based on a sampling rate, and/or number of sensors, of the sensor/receiver 906 of the NIBP sensor module 902, and/or other sensors, such as physiological sensors, that can be included on and/or communicate with the NIBP device 900. A typical ultrasound machine is used to image internal structures of the patient, in comparison, the ultrasound of the NIBP device 900 is used to generate data from which various parameters can be calculated. Due to the simplified nature, the number of processing channels 924 required in the NIBP device 900 can be significantly lower, or fewer, than the number of processing channels of a typical ultrasound imaging device. The number of processing channels 924 of the NIBP device 900 can be sufficient enough to allow for multiple sensors of the sensor/receiver 906 to generate NIBP signal(s)/data for processing. The number of sensors of the sensor/receiver 924 can allow for a wide area of patient tissue from which NIBP signal/data can be gathered/received. The processing of the NIBP signal/data can focus on a target vessel(s) based on the NIBP signal/data. To focus the ultrasound emitter 904 on the target vessel(s), the beamforming 922 can be used to direct the emitted ultrasound.

Figure 10:
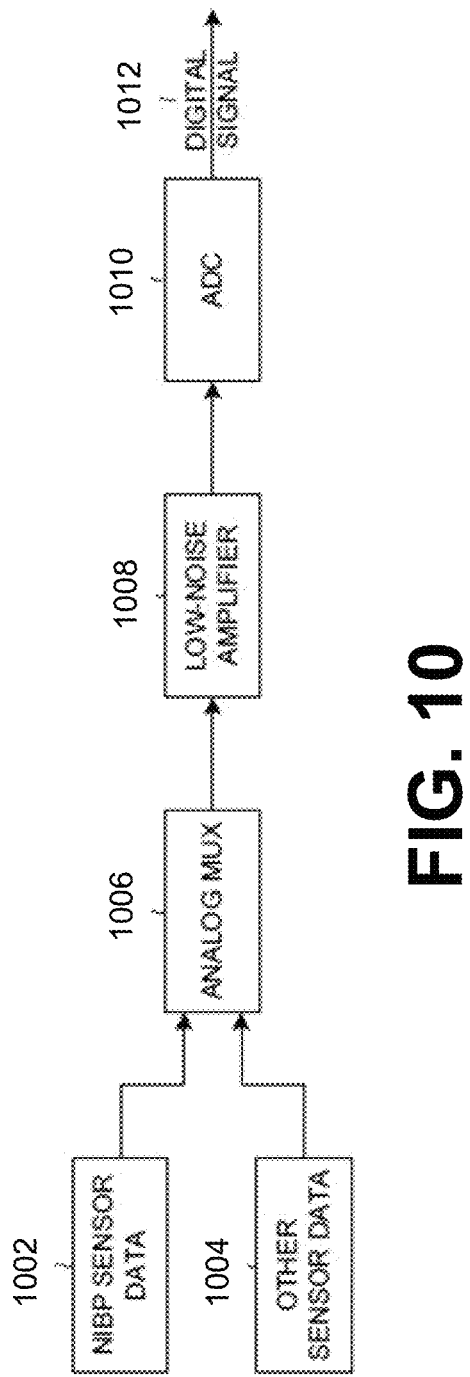
FIG. 10 is a block diagram of an example signal processing system.

The signal processing 916 can include an analog-to-digital converter (ADC), such as 1010 of FIG. 10, to convert the reflected ultrasound energy, received by the sensor/receiver 906, into a digital signal 1012. The sampling rate of the ADC 1010 can be relatively high, allowing the interleaving of sampling of other sensors, such as other physiological sensors. In this manner, a single ADC 1010 can be used in the sampling of not only the NIBP signal/data 1002, but also data 1004 from other sensors of, and/or communicating with, the NIBP device 900. The other sensors can require reduced sampling rates in comparison to the sampling rate of the sensor/receiver 906 and so can be combined or interleaved. An analog multiplexer (MUX) 1006 can be connected to the input of the ADC 1010 to combine the multiple inputs. The MUX can include any semiconductor switch, such as a metal-oxide semiconductor field-effect transistor (MOSFET) switch for example, or a microelectromechanical systems (MEMS) switch.

Certain sensors, such as ECG sensors, can require higher sampling rates compared to other sensors, in which case the sampling rate and/or interleaving of the ADC 1010 can be adjusted/modified to allow the NIBP signal/data 1002 and/or other sensor data 1004 to be sampled as needed/required. Further, a low-noise amplifier (LNA) 1008 can be disposed between the MUX 1006 and the ADC 1010, allowing the multiple sensors, such as those of the sensor/receiver 906, to share a single LNA 1008, which can reduce cost and/or complexity of the NIBP device 900. Alternatively, the MUX can be disposed between the LNA and the ADC if signal amplification is needed before entering the MUX. Additionally, multiple LNAs can be used that are each disposed to condition the signals that are input to a single MUX in some examples.

Beamforming 922 and/or other imaging techniques can be used to assist with collecting/generating the NIBP signal and/or data. Example beamforming techniques can include synthetic aperture imaging, plane-wave imaging, very fast Doppler imaging, adaptive beamforming, panoramic imaging and/or other beamforming techniques. Example other imaging techniques can include isonification techniques, such as harmonic imaging, coded pulses and/or FM pulses, and/or other signal/image processing techniques, such as compression, segmentation, pattern recognition, classification, and/or other techniques. Using the beamforming 922 and/or other imaging techniques, the NIBP sensor module 902 and/or the NIBP processing module 908 can map a patient's vasculature that is within the view of the ultrasound emitter(s) 904. Based on the vasculature, the beamforming and/or other imaging techniques can focus on a best vessel of opportunity of the mapped vasculature and can calculate real-time blood pressure 914 and/or vessel dynamics 910.

Figure 11:
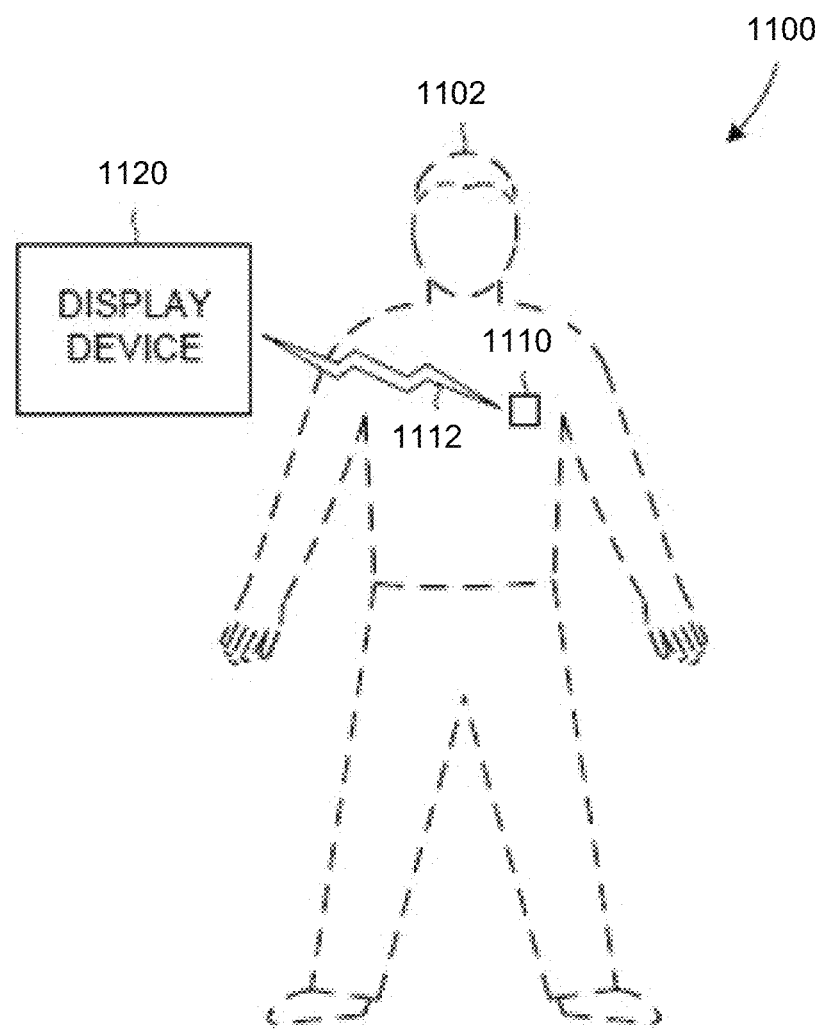
FIG. 11 is an example NIBP patch system.

FIG. 11 illustrates an example non-invasive blood pressure (NIBP) patch system 1100 that includes an NIBP patch 1110 that communicates 1112 with a display device 1120. The NIBP patch 1110 can calculate and/or monitor a blood pressure of a patient 1102 on which the NIBP patch 1110 is placed on, and/or affixed. The NIBP patch 1110 can include one or more emitters and sensors to radiate energy, such as ultrasound or light, into tissues of the patient 1102 and to sense the energy reflected therefrom. The reflected energy can be received and processed to determine blood pressure and/or vessel dynamics of the patient 1102. Additionally, the NIBP patch 1110 can include other sensors, such as physiological, temperature and/or motion sensors, to monitor other physiological parameters and/or status of the patient 1102 and/or status of the NIBP patch 1110.

The display device 1120 can receive, via communication 1112, the collected data, such as blood pressure, vessel dynamics, physiological and/or NIBP patch 1110 status data, for display. The display device 1120 can include a visual display, such as a screen, and/or an audible display, such as a speaker, to present the received data from the NIBP patch 1110. In addition to displaying the received data, the display device 1120 can also display data received from other sources, such as other devices/system monitoring and/or treating the patient 1102, to provide comprehensive display of patient 1102 data. Additionally, the display device 1120 can correlate the data displayed thereon to assist with monitoring and/or treating the patient 1102.

Data received by the display 1120 from the NIBP patch 1110 can also be transmitted by the display 1120, and/or NIBP patch 1110, to another external user, device and/or system. The display device 1120 can receive data from the NIBP patch 1110 continuously and/or in intervals. In an example, the display device 1120 can interrogate the NIBP patch 1110 to receive a response from the NIBP patch 1110 that includes the data.

Communications 1112 between the display device 1120 and the NIBP patch 1110 can include data transmissions and, optionally, power transmissions, such as via a near-field communication (NFC). In an example, the display device 1120 can broadcast a power signal, such as a radio transmission, that can be received by the NIBP patch 1110 to induce a current in the NIBP patch 1110 that powers one or more functions/features of the NIBP patch 1110. In response, the NIBP patch 1110 can perform the one or more functions/features and/or transmit collected data from the NIBP patch 1110 to the display device 1120. This can allow the NIBP patch 1110 to operate in a low/reduced-power mode when not receiving the power signal from the display device 1120, operate when receiving the power signal from the display device 1120 and/or transmit data in response to the power, or other, signal from the display device 1120.

It will be appreciated that variants of the above-disclosed and other features and functions, or alternatives thereof, may be combined into many other different devices, systems and/or applications. Various presently unforeseen or unanticipated alternatives, modifications, variations, or improvements therein may be subsequently made by those skilled in the art, which are also intended to be encompassed by the following claims.

What is claimed is:

1. A medical device, comprising:
    an emitter configured to emit a signal toward a blood vessel of a patient, the signal comprising electromagnetic waves or mechanical waves;
    a detector configured to receive a reflection of the signal from the blood vessel or blood flowing through the blood vessel; and
    a processor configured to:
        determine a metric by analyzing the reflection;
        determine, by analyzing an electrocardiogram (ECG) of the patient and the metric, whether the patient has pulseless electrical activity (PEA);
        output an indication of whether the patient has PEA;
        determine, by analyzing the reflection, a geometry of the blood vessel;
        determine a severity score indicating a severity of a condition of the patient by analyzing the geometry of the blood vessel and a velocity of the blood flowing through the blood vessel; and
        output the severity score.

2. The medical device of claim 1, wherein the signal comprises ultrasound or light.

3. The medical device of claim 1, wherein the metric comprises a blood pressure of the patient.

4. The medical device of claim 1, wherein the processor is configured to determine a metric by analyzing the reflection by:
    determining a pulse wave velocity of the blood vessel;
    determining a blood velocity of the blood flowing through the blood vessel; and
    determining a product of the pulse wave velocity, the blood velocity, and a density of the blood, the metric being equal to the product,
    wherein the pulse wave velocity or the blood velocity is determined by analyzing the reflection.

5. The medical device of claim 1, wherein the processor is further configured to:
    determine, by analyzing the reflection, the velocity of the blood flowing through the blood vessel; and
    identify the condition of the patient by analyzing the geometry of the blood vessel or the velocity of the blood flowing through the blood vessel.

6. The medical device of claim 5, wherein the condition of the patient comprises an aneurysm, a return of spontaneous circulation (ROSC), or a vascular blockage.

7. The medical device of claim 1, wherein the blood vessel is located in a neck or in an abdomen of the patient.

8. A method, comprising:
    emitting a signal toward a blood vessel of a patient, the signal comprising electromagnetic waves or mechanical waves;
    detecting a reflection of the signal from the blood vessel or blood flowing through the blood vessel;
    determining a metric by analyzing the reflection;

determining, by analyzing an electrocardiogram (ECG) of the patient and the metric, whether the patient has pulseless electrical activity (PEA); and
outputting an indication of whether the patient has PEA,
wherein determining the metric by analyzing the reflection comprises:
determining a pulse wave velocity of the blood vessel, and
determining an instantaneous blood velocity of the blood flowing through the blood vessel, wherein the pulse wave velocity and the instantaneous blood velocity are determined simultaneously.

9. The method of claim 8, wherein the signal comprises ultrasound or light.

10. The method of claim 8, wherein the metric comprises a blood pressure of the patient.

11. The method of claim 8, wherein determining the metric by analyzing the reflection further comprises:
determining a product of the pulse wave velocity, the instantaneous blood velocity, and a density of the blood, the metric being equal to the product,
wherein the pulse wave velocity or the instantaneous blood velocity is determined based on the reflection.

12. The method of claim 8, further comprising:
determining, by analyzing the reflection, a geometry of the blood vessel or a velocity of the blood flowing through the blood vessel; and
identifying a condition of the patient by analyzing the geometry of the blood vessel or the velocity of the blood flowing through the blood vessel.

13. The method of claim 11, further comprising:
determining, by analyzing a geometry of the blood vessel or the velocity of the blood flowing through the blood vessel, a severity score indicating a severity of a condition of the patient; and
outputting the severity score.

14. The method of claim 11, wherein a condition of the patient comprises an aneurysm, a return of spontaneous circulation (ROSC), or a vascular blockage.

15. The method of claim 8, wherein the blood vessel is located in a neck or in an abdomen of the patient.

16. The medical device of claim 1, further comprising:
a sensor configured to detect the ECG of the patient,
wherein:
the signal comprises an ultrasound signal,
determining the metric based on the reflection comprises:
determining a pulse wave velocity by analyzing the reflection of the ultrasound signal from the blood vessel;
determining a velocity of the blood flowing through the blood vessel by analyzing the reflection of the ultrasound signal from the blood flowing through the blood vessel; and
determining a blood pressure of the patient as a function of the pulse wave velocity and the velocity of the blood flowing through the blood vessel, and
determining whether the patient has PEA further comprises analyzing the blood pressure.

17. The medical device of claim 1, wherein the condition of the patient comprises an aneurysm, a return of spontaneous circulation (ROSC), or a vascular blockage.

18. The medical device of claim 16, wherein the blood vessel is located in a neck or in an abdomen of the patient.

19. A medical device, comprising:
an emitter configured to emit a signal toward a blood vessel of a patient, the signal comprising electromagnetic waves or mechanical waves;
a detector configured to receive a reflection of the signal from the blood vessel or blood flowing through the blood vessel; and
a processor configured to:
determine a metric by analyzing the reflection;
determine, by analyzing an electrocardiogram (ECG) of the patient and the metric, whether the patient has pulseless electrical activity (PEA); and
output an indication of whether the patient has PEA,
wherein determining the metric by analyzing the reflection comprises:
determining a pulse wave velocity of the blood vessel, and
determining an instantaneous blood velocity of the blood flowing through the blood vessel, wherein the pulse wave velocity and the instantaneous blood velocity are determined simultaneously.

* * * * *